US010606351B2

(12) United States Patent
Tsurumi

(10) Patent No.: US 10,606,351 B2
(45) Date of Patent: Mar. 31, 2020

(54) INFORMATION PROCESSING APPARATUS, INFORMATION PROCESSING METHOD, AND COMPUTER READABLE RECORDING MEDIUM

(71) Applicant: SONY CORPORATION, Tokyo (JP)

(72) Inventor: Shingo Tsurumi, Saitama (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/069,225

(22) PCT Filed: Nov. 7, 2016

(86) PCT No.: PCT/JP2016/082935
§ 371 (c)(1),
(2) Date: Jul. 11, 2018

(87) PCT Pub. No.: WO2017/130514
PCT Pub. Date: Aug. 3, 2017

(65) Prior Publication Data
US 2019/0018487 A1 Jan. 17, 2019

(30) Foreign Application Priority Data
Jan. 27, 2016 (JP) ................. 2016-012976

(51) Int. Cl.
G09G 5/00 (2006.01)
G06F 3/01 (2006.01)
(Continued)

(52) U.S. Cl.
CPC .............. *G06F 3/013* (2013.01); *A61B 3/113* (2013.01); *G06F 3/002* (2013.01); *G06F 3/0487* (2013.01);
(Continued)

(58) Field of Classification Search
CPC . G06F 3/002; G06F 3/01; G06F 3/013; G06F 3/0484; G06F 3/0487; G06T 7/70;
(Continued)

(56) References Cited

U.S. PATENT DOCUMENTS 10,165,949 B2 * 1/2019 Tzvieli ................. G01J 5/0265
2002/0118339 A1 * 8/2002 Lowe ..................... A61B 3/032
351/209
(Continued)

FOREIGN PATENT DOCUMENTS

CN 106028913 A 10/2016
JP 2015-153302 A 8/2015
(Continued)

OTHER PUBLICATIONS

International Search Report and Written Opinion of PCT Application No. PCT/JP2016/082935, dated Feb. 7, 2017, 07 pages of ISRWO.

Primary Examiner — Joe H Cheng
(74) Attorney, Agent, or Firm — Chip Law Group

(57) ABSTRACT

Provided is an information processing apparatus including a processing unit that performs a derivation process of deriving a relative positional relation between a user and a display screen such that a calibration position is within an angle of view of the display screen, the calibration position being stared by the user of a line of sight detection target when sampling data for calibration of a line of sight is acquired.

14 Claims, 13 Drawing Sheets

(51) Int. Cl.
*G06F 3/16* (2006.01)
*A61B 3/113* (2006.01)
*G06F 3/00* (2006.01)
*G06F 3/0487* (2013.01)
*G06T 7/73* (2017.01)
*A63F 13/22* (2014.01)
*A63F 13/213* (2014.01)
*A63F 13/212* (2014.01)

(52) U.S. Cl.
CPC .................. *G06F 3/16* (2013.01); *G06T 7/74* (2017.01); *A63F 13/212* (2014.09); *A63F 13/213* (2014.09); *A63F 13/22* (2014.09); *G06T 2207/30201* (2013.01); *G06T 2207/30204* (2013.01)

(58) Field of Classification Search
CPC ............. G06T 7/74; G06T 2207/30201; A63F 13/213; A61B 3/113
See application file for complete search history.

(56) References Cited

U.S. PATENT DOCUMENTS

| | | | | |
|---|---|---|---|---|
| 2010/0097580 A1* | 4/2010 | Yamamoto | ........... | G02B 26/101 353/69 |
| 2012/0223884 A1* | 9/2012 | Bi | .......... | G06F 1/1694 345/158 |
| 2013/0265227 A1* | 10/2013 | Julian | ................. | G06F 3/04812 345/157 |
| 2015/0109204 A1* | 4/2015 | Li | ........... | G06F 3/011 345/156 |
| 2015/0116473 A1* | 4/2015 | Yasuda | .............. | G06Q 30/0242 348/78 |
| 2015/0234461 A1 | 8/2015 | Suzuki et al. | | |
| 2015/0358594 A1* | 12/2015 | Marshall | ................. | G06F 3/013 345/419 |
| 2016/0086338 A1 | 3/2016 | Nagamatsu et al. | | |
| 2016/0195926 A1* | 7/2016 | Imoto | ..................... | G06F 3/012 382/103 |
| 2016/0217794 A1* | 7/2016 | Imoto | ..................... | G06F 3/167 |
| 2016/0262608 A1* | 9/2016 | Krueger | ................. | A61B 3/0041 |
| 2016/0300108 A1* | 10/2016 | Willis | .................. | G06K 9/0061 |
| 2016/0342205 A1 | 11/2016 | Shigeta et al. | | |
| 2018/0309937 A1* | 10/2018 | Yoshino | ............. | G06K 9/00744 |
| 2018/0367773 A1* | 12/2018 | Holub | ................... | G01J 3/0272 |

FOREIGN PATENT DOCUMENTS

| | | |
|---|---|---|
| WO | 2014/188727 A1 | 11/2014 |
| WO | 2015/125243 A1 | 8/2015 |

\* cited by examiner

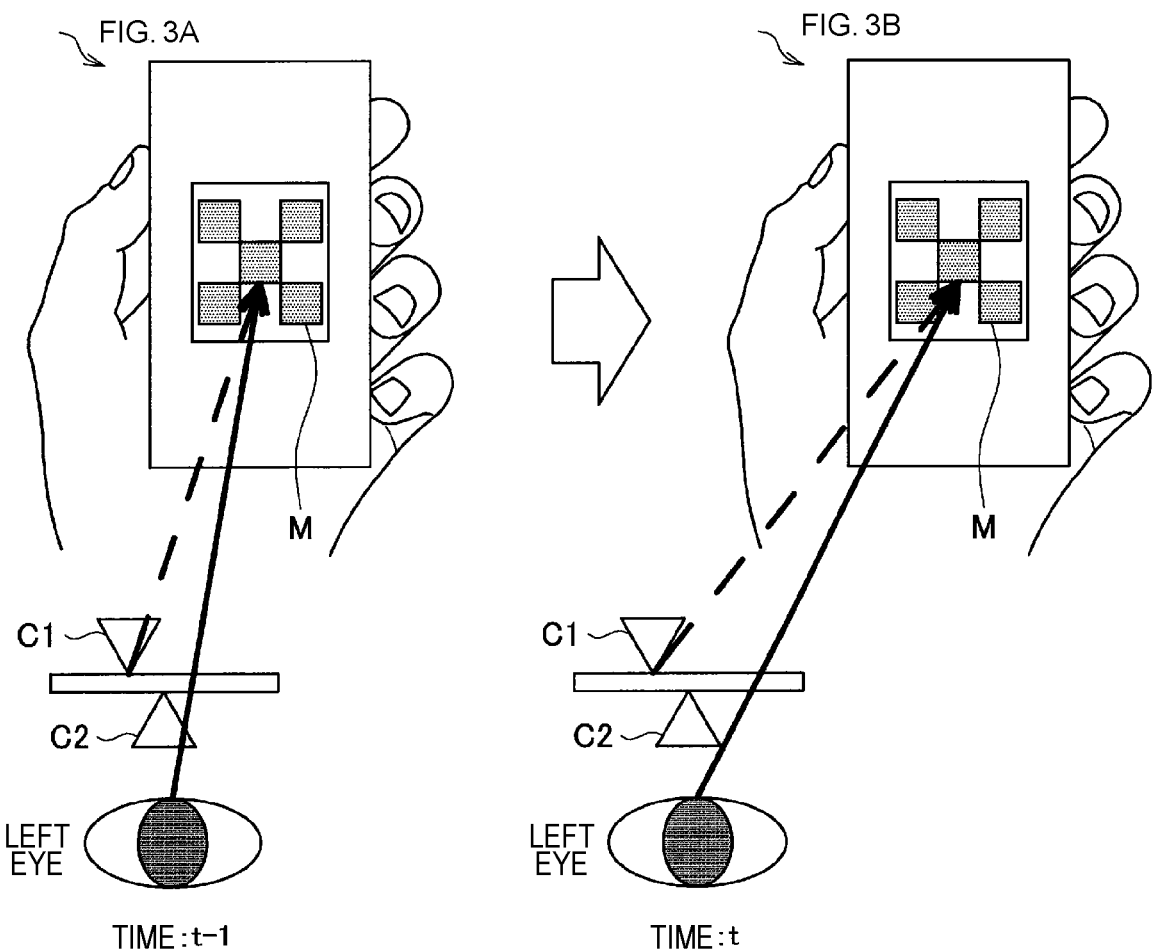

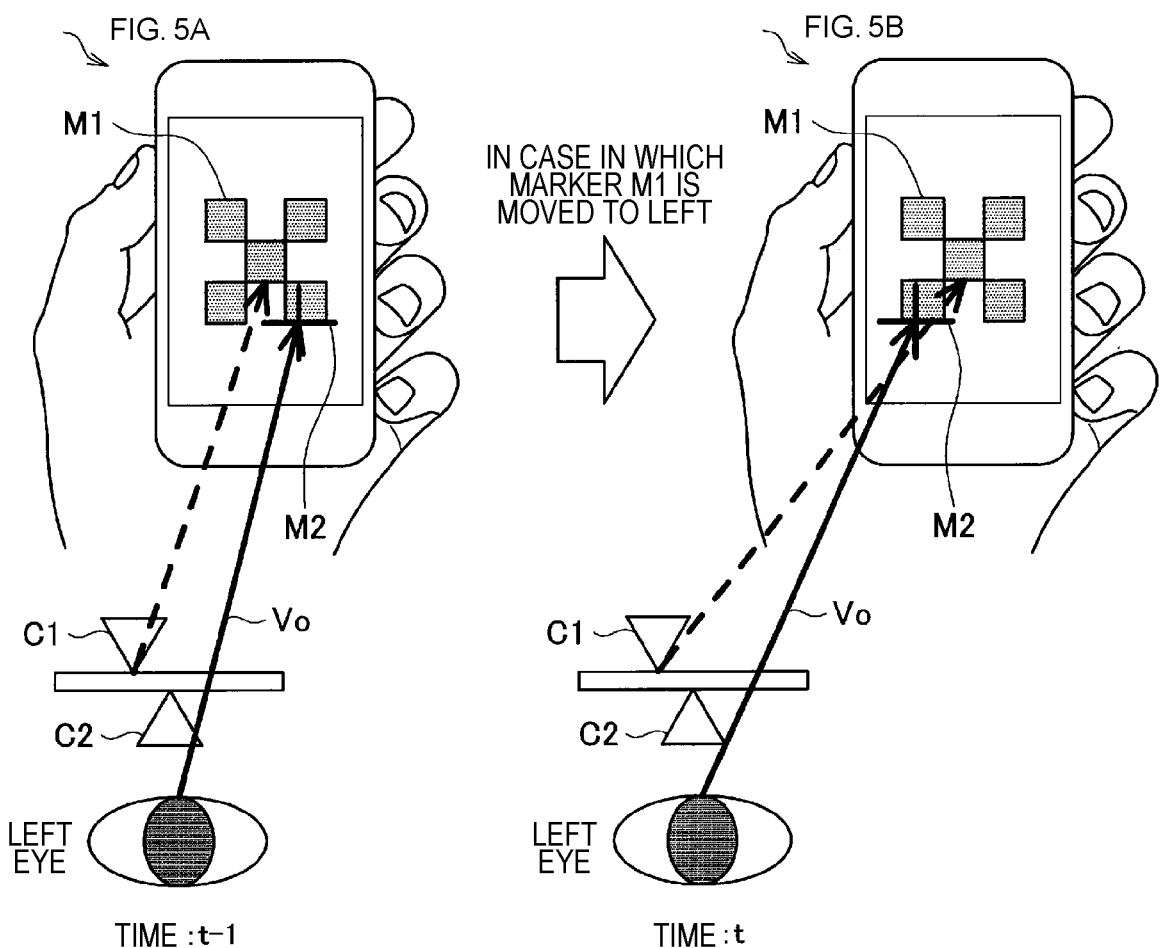

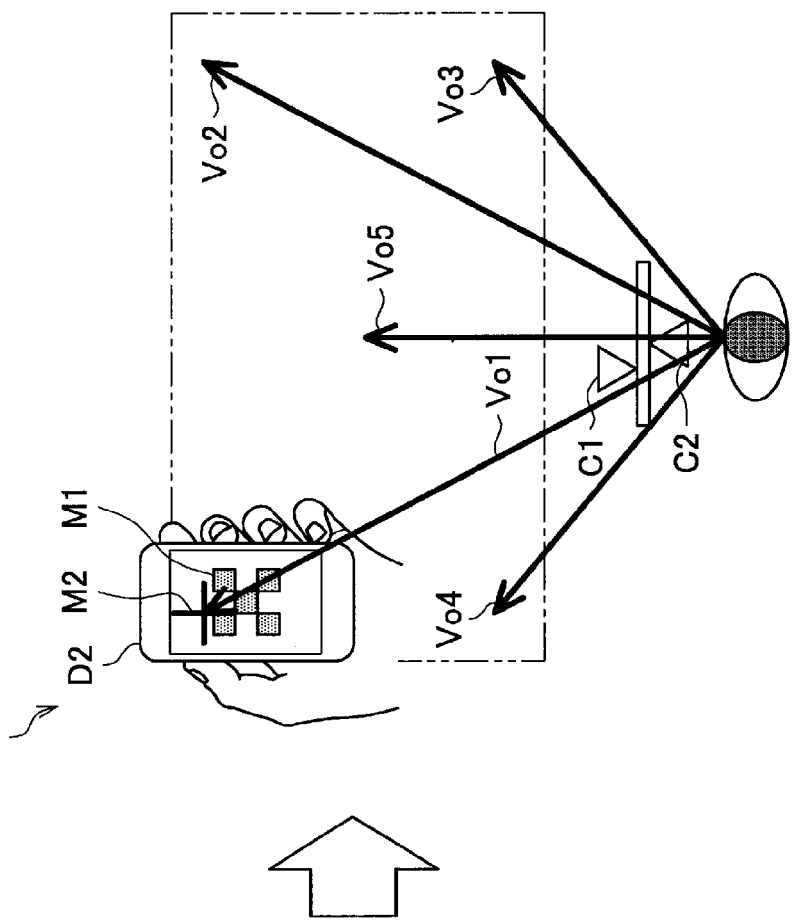
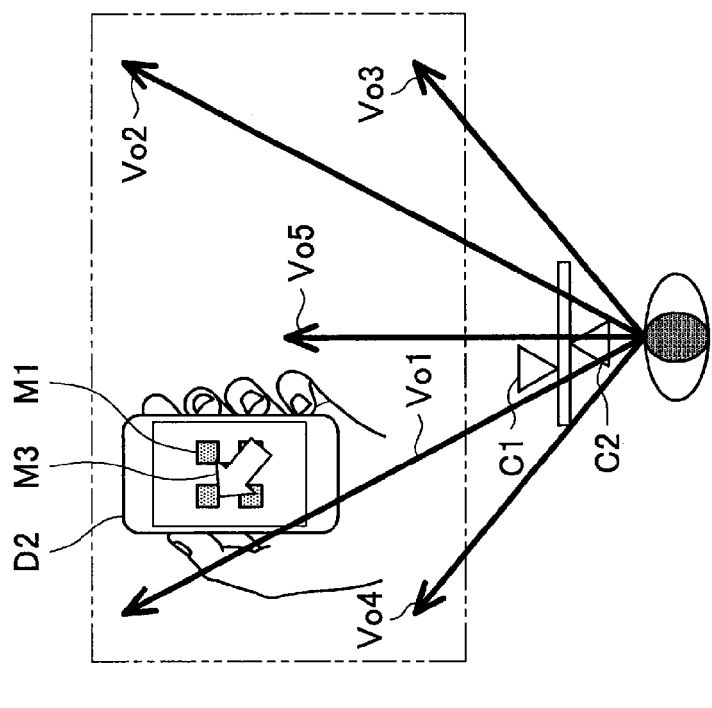

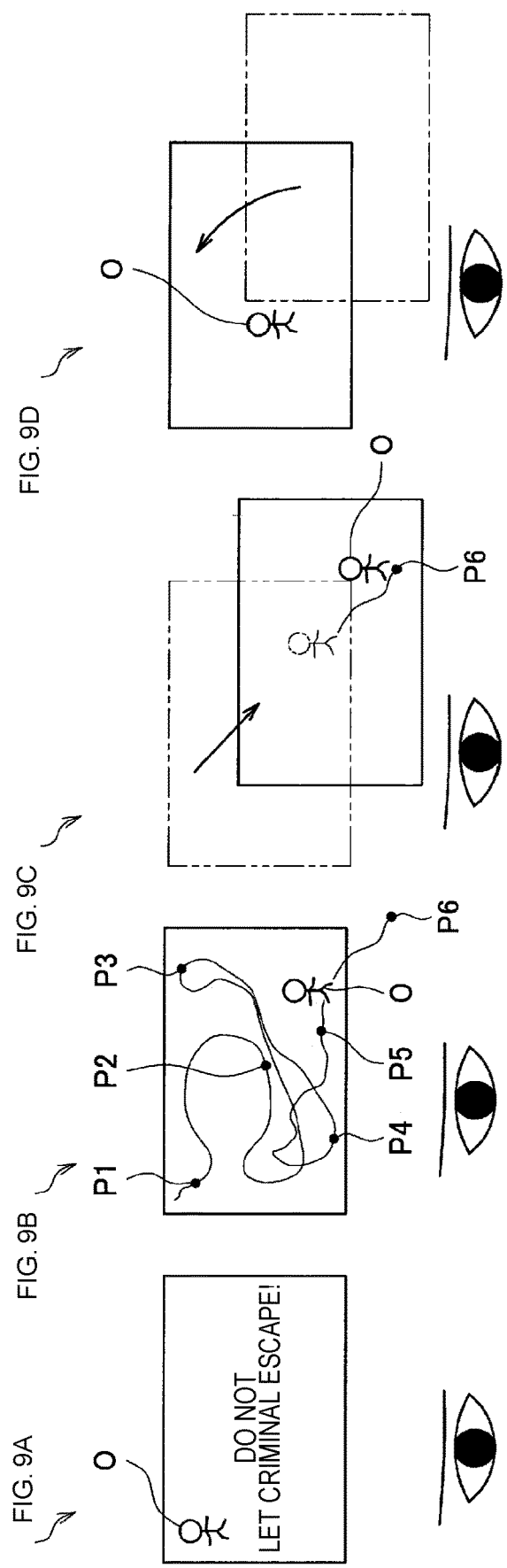

INFORMATION PROCESSING APPARATUS, INFORMATION PROCESSING METHOD, AND COMPUTER READABLE RECORDING MEDIUM

CROSS REFERENCE TO RELATED APPLICATIONS

This application is a U.S. National Phase of International Patent Application No. PCT/JP2016/082935 filed on Nov. 7, 2016, which claims priority benefit of Japanese Patent Application No. JP 2016-012976 filed in the Japan Patent Office on Jan. 27, 2016. Each of the above-referenced applications is hereby incorporated herein by reference in its entirety.

TECHNICAL FIELD

The present disclosure relates to an information processing apparatus, an information processing method, and a computer readable recording medium having a program recorded therein.

BACKGROUND ART

As a method used for detection of a line of sight, for example, there is a "method using a corneal reflex technique (a pupil corneal reflex technique) using a corneal reflection image (also referred to as a Purkinje image') formed such that light from a light source such as an infrared light emitting diode (IR LED) is reflected by a cornea" or the like.

Here, there may be an error between a position or the like at which a user is estimated to be staring from a detection result of the line of sight obtained by using the above-described technique and a position at which the user is actually staring or the like. For this reason, the detection result of the line of sight detected using the above-described technique is calibrated to reduce the error, and the position at which the user is staring or the like is estimated using the calibrated detection result of the line of sight.

Under such circumstances, a technique related to the calibration of the line of sight has been developed. As a technique related to the calibration of the line of sight, for example, a technique described in Patent Literature 1 is known.

CITATION LIST

Patent Literature

Patent Literature 1: JP 2015-152939A

DISCLOSURE OF INVENTION

Technical Problem

As a method of performing calibration of a line of sight, there is a method of performing calibration of a line of sight using, for example, a wearable device worn on the head of a user such as a head mounted display or eyewear. As a specific example, as a method of performing calibration of a line of sight using a wearable device worn on the head, for example, there are the following methods (a) and (b). (a) An apparatus that performs calibration causes a marker to be displayed on a calibration position on a display screen of a display device installed in a wearable device worn on a user's head, causes the user to stare at the marker, and acquires sampling data for the calibration of the line of sight. Then, the apparatus calibrates the detection result of the line of sight in accordance with calibration information (to be described later) obtained on the basis of the acquired sampling data. (b) An apparatus that performs calibration causes a marker printed on a sheet to be imaged through an imaging device (hereinafter referred to as an "outward imaging device") which is installed in a wearable device worn on a user's head and images a direction opposite to a face side of the user when worn by the user. Then, the apparatus calibrates the detection result of the line of sight in accordance with calibration information (to be described later) based on sampling data for the calibration of the line of sight obtained by detecting the marker from the acquired captured image.

However, in the method of (a), if the wearable device worn on the head does not include the display device capable of displaying the marker on the display screen, the sampling data is unable to be acquired, and the detection result of the line of sight is unable to be calibrated as well. Further, in the method of (b), since a positional relation between the outward imaging device and the sheet on which the marker is printed is not necessarily constant, the sampling data may be unable to be stably acquired.

The present disclosure discloses an information processing apparatus, an information processing method, and a computer readable recording medium having a program recorded therein, which are novel and improved and capable of improving stability of acquisition of the sampling data for the calibration of the line of sight.

Solution to Problem

According to the present disclosure, there is provided an information processing apparatus including a processing unit configured to perform a derivation process of deriving a relative positional relation between a user and a display screen such that a calibration position is within an angle of view of the display screen, the calibration position being stared by the user of a line of sight detection target when sampling data for calibration of a line of sight is acquired.

In addition, according to the present disclosure, there is provided an information processing method executed by an information processing apparatus, the method including a step of deriving a relative positional relation between a user and a display screen such that a calibration position is within an angle of view of the display screen, the calibration position being stared by the user of a line of sight detection target when sampling data for calibration of a line of sight is acquired.

In addition, according to the present disclosure, there is provided a computer readable storage medium having a program stored therein, the program causing a computer to implement a function of deriving a relative positional relation between a user and a display screen such that a calibration position is within an angle of view of the display screen, the calibration position being stared by the user of a line of sight detection target when sampling data for calibration of a line of sight is acquired.

Advantageous Effects of Invention

According to the present disclosure, it is possible to improve the stability of the acquisition of the sampling data for the calibration of the line of sight.

Note that the effects described above are not necessarily limitative. With or in the place of the above effects, there

BRIEF DESCRIPTION OF DRAWINGS

FIGS. 3A and 3B are explanatory diagrams for describing an example of a process related to a method of calibrating a detection result of a line of sight.

FIGS. 5A and 5B are explanatory diagrams for describing an example of an information processing method according to the present embodiment.

FIGS. 6A and 6B are explanatory diagrams for describing an example of a derivation process related to an information processing method according to the present embodiment.

FIGS. 9A, 9B, 9C, and 9D are explanatory diagrams for describing an example of a derivation process related to an information processing method according to the present embodiment.

MODE(S) FOR CARRYING OUT THE INVENTION

Figure 1:
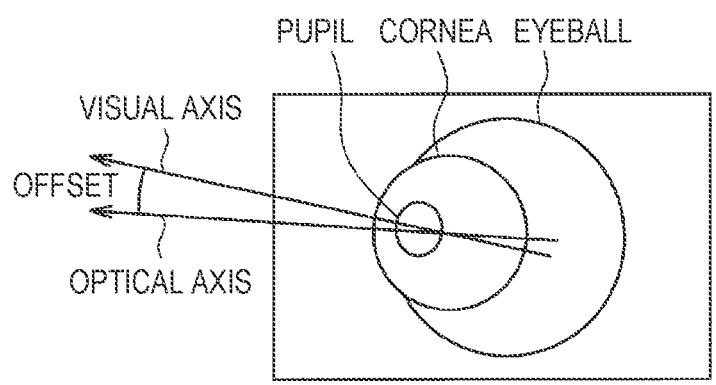
FIG. 1 is an explanatory diagram for describing an example of a method of calibrating a detection result of a line of sight.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, the following description will proceed in the following order.
1. Information processing method according to present embodiment
2. Information processing apparatus according to present embodiment
3. Program according to present embodiment
4. Computer readable recording medium having program recorded therein according to present embodiment (Information Processing Method According to Present Embodiment)

First, an information processing method according to the present embodiment will be described. The following description will proceed with an example in which a process related to the information processing method according to the present embodiment is performed by the information processing apparatus according to the present embodiment.

[1] Method of Calibrating Detection Result of Line of Sight

First, a method of calibrating the detection result of the line of sight will be described. The following description will proceed with an example of a method of calibrating the detection result of the line of sight in a case in which the line of sight is detected by the method using the corneal reflex technique.

FIG. 1 is an explanatory diagram for describing an example of the method of calibrating the detection result of the line of sight, and illustrates an example of a captured image obtained by imaging an eye of a user who is a line of sight detection target. Hereinafter, the user who is the line of sight detection target is also referred to simply as a "user."

Axes related to the line of sight of the user include an optical axis and a visual axis as illustrated in FIG. 1.

Here, the optical axis is a corneal normal passing through the center of the pupil and corresponds to, for example, a line connecting a conical center position (a three-dimensional position of the center of the cornea center (the center of curvature of the cornea)) with a pupil center position (a three-dimensional position of the center of the pupil). The optical axis can be estimated, for example, using a 3D eyeball model. On the other hand, the visual axis is unable to be estimated using the 3D eyeball model in the same way as the optical axis.

Therefore, examples of the result of detection of the line of sight using the corneal reflex technique include detection results based on the optical axis such as one or more of a direction indicated by a detected optical axis, a vector indicating the detected optical axis, and a position at which the user is looking that is specified on the basis of the detected optical axis. Hereinafter, the vector indicating the optical axis indicated by the detection result of the line of sight is referred to as an "optical axis vector."

The visual axis is a line connecting a nodal point (a central posterior surface of a crystalline lens) with a central fovea and corresponds to an axis at which the user (person) is actually looking. The visual axis and the optical axis do not coincide with each other as illustrated in FIG. 1, and the visual axis is inclined about 4[°] to 8[°] with respect to the optical axis. Further, there are individual differences in an inclination of the visual axis with respect to the optical axis.

In order to further reduce a deviation (an "offset" illustrated in FIG. 1) of the visual axis from the optical axis, calibration is performed. The calibration is performed, for example, for each eye of the user.

Further, as described above, the visual axis is unable to be estimated using the eyeball 3D model in the same way as the optical axis. Therefore, the visual axis is estimated by calibrating the optical axis in accordance with, for example, the following procedure.

A difference (offset) between the optical axis vector obtained when the user is caused to look at a calibration position and a vector connecting a reference position corresponding to an eyeball with the calibration position (hereinafter referred to as a "correct solution vector") is obtained, and the obtained difference is recorded and held in a recording medium.

The optical axis vector is corrected using calibration information (to be described later) obtained on the basis of the difference.

Here, examples of the reference position corresponding to the eyeball include a position of the eyeball and a position of an outward imaging device installed in a wearable device worn on the head. Further, the difference (offset) between the optical axis vector and the correct solution vector corresponds to sampling data for the calibration of the line of sight.

An example of a process related to the method of calibrating the detection result of the line of sight will be described using a process according to the method of (a) (the method of causing a marker to be displayed on a display screen installed in the wearable device worn on the head) and the method of (b) (the method using a marker printed on a sheet) as an example.

Figure 2A:
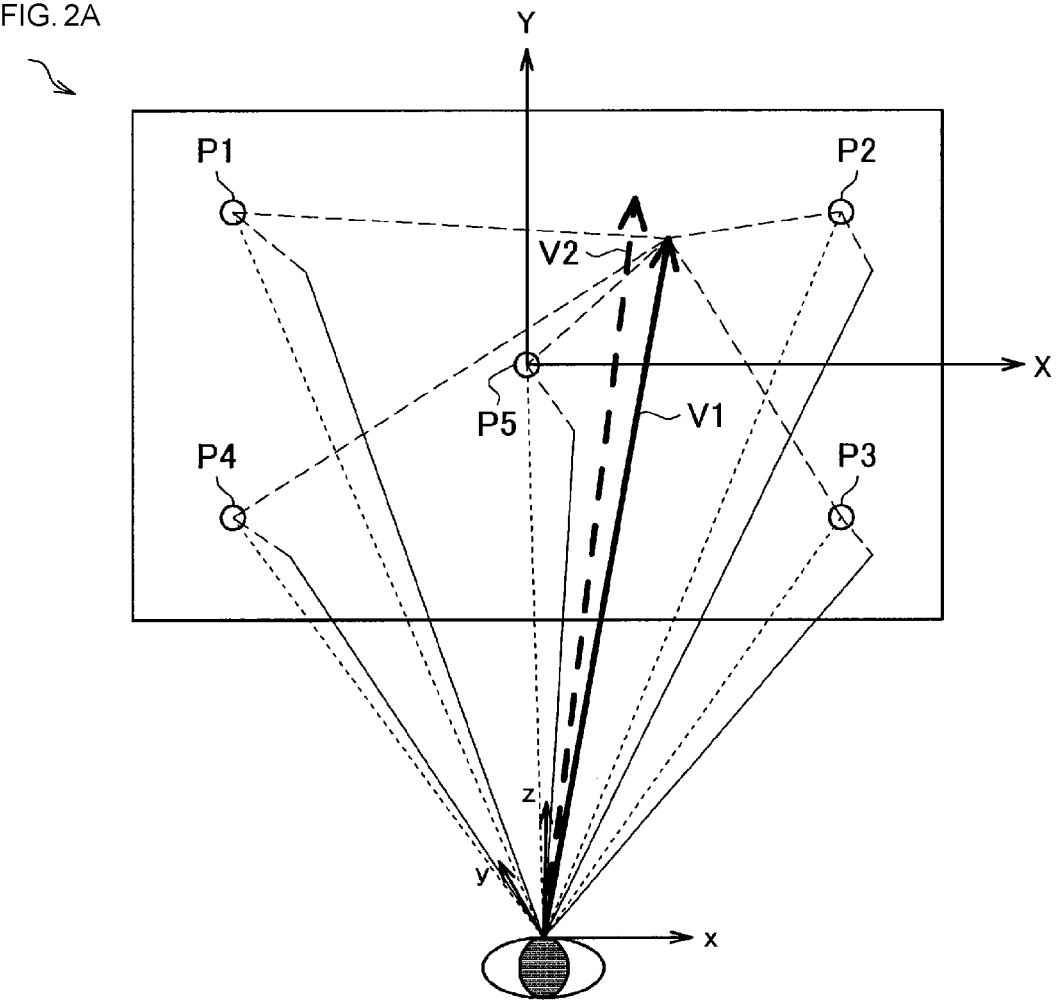
FIGS. 2A and 2B are explanatory diagrams for describing an example of a process related to a method of calibrating a detection result of a line of sight.
Figure 2B:
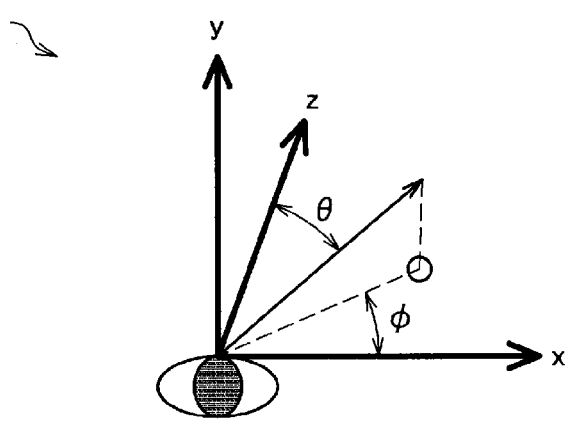

FIGS. 2A and 2B are explanatory diagrams for describing an example of a process related to the method of calibrating the detection result of the line of sight, that is, a diagram for describing an example of the process according to the method of (a) (the method of causing the marker to be displayed on the display screen installed in the wearable device worn on the head). FIG. 2A illustrates an example of a display screen in glasses type eyewear (an example of the wearable device worn on the head). Further, FIG. 2B illustrates an example of a coordinate system associated with the eye.

The user is caused to look at each of calibration positions P1, P2, P3, P4, and P5 on the display screen, and a difference ($\Delta\varphi n$, $\Delta\theta n$) (n is a number assigned to the calibration position) between the optical axis vector and the correct solution vector in each case is held in a recording medium. Here, $\Delta\varphi n$ indicates the difference between $\varphi n$ of the optical axis vector and $\varphi n$ of the correct solution vector. Further, $\Delta\theta n$ indicates a difference between $\theta n$ of the optical axis vector and $\theta n$ of the correct solution vector.

In a case in which an optical axis vector V1 is calibrated at a certain time point, the optical axis vector V1 is calibrated using a calibration parameter ($\Delta\varphi$, $\Delta\theta$) obtained by integrating the differences ($\Delta\varphi n$, $\Delta\theta n$) between the optical axis vector and the correct solution vector corresponding to the calibration positions P1, P2, P3, P4, and P5. The integrating of the differences ($\Delta\varphi n$, $\Delta\theta n$) between the optical axis vector and the correct solution vector corresponding to a plurality of calibration positions P1, P2, P3, P4, and P5 is, for example, obtaining an average value of the differences ($\Delta\varphi n$, $\Delta\theta n$) between the optical axis vector and the correct solution vector corresponding to a plurality of calibration positions P1, P2, P3, P4, and P5.

Here, the calibration parameter ($\Delta\varphi$, $\Delta\theta$) corresponds to an example of the calibration information based on the sampling data. The calibration information according to the present embodiment can be obtained for each eye of the user, for example, by calculating the calibration parameter ($\Delta\varphi$, $\Delta\theta$) for each eye of the user. Further, it is also possible to use the calibration information obtained for one eye as the calibration information corresponding to the other eye.

For example, $\Delta\varphi$ in the calibration parameter ($\Delta\varphi$, $\Delta\theta$) is calculated by the following Formula 1. Here, "$r_n$" in the following Formula 1 indicates a distance between the position of the eye of the user and the calibration position, and Formula 1 indicates the calibration parameter weighted by the distance. The distance between the position of the eye of the user and the calibration position can be obtained, for example, on the basis of an "estimation based on the captured image captured by the outward imaging device installed in the glasses type eyewear (an example of the wearable device worn on the head)," a "detection result of a distance sensor of an arbitrary scheme," or the like.

[Math. 1]

$$\begin{cases} \Delta\phi = a \cdot \Sigma_n \dfrac{\Delta\phi_n}{r_n} \\ a = \dfrac{1}{\Sigma_n \dfrac{1}{r_n}} \end{cases} \quad \text{(Formula 1)}$$

Further, $\Delta\theta$ in the calibration parameter ($\Delta\varphi$, $\Delta\theta$) can be calculated as in Formula 1.

Further, it will be appreciated that the example of calculating the calibration parameter ($\Delta\varphi$, $\Delta\theta$) (an example of the calibration information) is not limited to the above example.

FIGS. 3A and 3B are explanatory diagrams for describing an example of a process related to the method of calibrating the detection result of the line of sight, that is, a diagram for describing an example of a process according to the method of (b) (the method using the marker printed on the sheet).

Reference numeral C1 in FIGS. 3A and 3B indicate an outward imaging device installed in the glasses type eyewear. Further, reference numeral C2 in FIGS. 3A and 3B indicate an imaging device (hereinafter also referred to as an "inward imaging device") that images the eye of the user when the glasses type eyewear in which it is installed is worn by the user. The outward imaging device is used to generate a captured image which is used to detect an object such as the marker. Further, the inward imaging device is used to generate a captured image which is used to detect the line of sight of the user. Hereinafter, the outward imaging device is denoted as an "outward imaging device C1," and the inward imaging device is denoted as an "inward imaging device C2."

FIGS. 3A and 3B illustrate an example of imaging a marker M printed on a sheet through the outward imaging device C1. FIG. 3A illustrates a state at a time t−1, and FIG. 3B illustrates a state at a time t.

In the method using the marker printed on the sheet, as described above, the sampling data is obtained by detecting the marker M from the captured image generated by the imaging performed by the outward imaging device C1. Specifically, in the method using the marker printed on the sheet, for example, a position of the outward imaging device C1 is set as the reference position corresponding to the eyeball, and a center position of the marker M is set as the calibration position. Then, a difference between the optical axis vector and the correct solution vector connecting the position of the outward imaging device C1 (an example of the reference position corresponding to the eyeball) with the center position of the marker M (an example of the calibration position) is obtained as the sampling data for the calibration of the line of sight.

In the method using the marker printed on the sheet, it is determined that the marker M is stationary by detecting the marker M from a plurality of captured images, and in a case in which the marker M is determined to be stationary, the optical axis vectors at a plurality of time points are acquired together, and the sampling data is obtained. Then, the calibration parameter ($\Delta\varphi$, $\Delta\theta$) (an example of the calibration information) is calculated similarly to the process according to the method of (a) (the method of causing the marker to be displayed on the display screen installed in the wearable device worn on the head), and the optical axis vector at a certain time point is calibrated using the calculated calibration parameter ($\Delta\varphi$, $\Delta\theta$).

[2] Factors Inhibiting Stable Acquisition of Sampling Data for Calibration of Line of Sight In each of the method of (a) (the method of causing the marker to be displayed on the display screen installed in the wearable device worn on the head) and the method of (b) (the method using the marker printed on the sheet), the sampling data is acquired as described above. Further, in each of the method of (a) (the method of causing the marker to be displayed on the display screen installed in the wearable device worn on the head) and the method of (b) (the method using the marker printed on the sheet), the optical axis vector is calibrated in accordance with the calibration information based on the acquired sampling data.

However, in a case in which the method of (a) (the method of causing the marker to be displayed on the display screen installed in the wearable device worn on the head) is used, the sampling data is unable to be acquired unless the wearable device worn on the head includes the display device capable of displaying the marker on the display screen as described above. Further, the method of (a) (the method of causing the marker to be displayed on the display screen installed in the wearable device worn on the head) is a method which can be applied only when the wearable device worn on the head includes the display device capable of displaying the marker on the display screen.

Further, in the method of (b) (the method using the marker printed on the sheet), the position of the marker M with respect to the outward imaging device C1 is not necessarily constant. Further, for example, as illustrated in FIG. 3A and FIG. 3B, if the marker M moves with respect to the outward imaging device C1, the correct solution vector changes with the movement of the marker M with respect to the outward imaging device C1. Further, in a case in which the marker M moves with respect to the outward imaging device C1 as illustrated in FIG. 3A and FIG. 3B, since the correct solution vectors at the respective time points are different, the calibration information is unable to be obtained on the basis of a plurality of pieces of sampling data obtained from the same correct solution vector.

Further, in a case in which the calibration information is obtained while regarding different correct solution vectors as being independent of one another, the accuracy of the estimation result of the visual axis obtained by calibrating the detection result of the line of sight is unlikely to be stable.

[3] Process Related to Information Processing Method According to Present Embodiment

[3-1] Overview of Process Related to Information Processing Method According to Present Embodiment In this regard, the information processing apparatus according to the present embodiment performs a derivation process of deriving a relative positional relation between the user of the line of sight detection target and the display screen so that the calibration position is positioned within the angle of view of the display screen.

Here, examples of the display screen according to the present embodiment include a "display screen of a display device installed various apparatuses such as smartphones," a "region of a wall onto which an image is projected by an image projecting device such as a projector."

Further, the calibration position according to the present embodiment is a position at which the user is caused to stare at when the sampling data for the calibration of the line of sight is acquired. Hereinafter, the sampling data for the calibration of the line of sight is also referred to as simply as "sampling data."

As the calibration position according to the present embodiment, for example, an intersection point of a reference vector corresponding to a forward direction of the face of the user and a plane including the display screen may be used.

The reference vector according to the present embodiment is a fixed vector set in a coordinate system associated with the face of the user. As the reference vector according to the present embodiment, for example, one or more vectors which have a position of an origin of the coordinate system corresponding to the face of the user as a starting point and correspond to the number of calibration positions may be used.

As the coordinate system associated with the face of the user, for example, a "fixed coordinate system in which a position at which the inward imaging device C2 is installed (or a position at which the outward imaging device C1 is installed) is used as the origin in the wearable device worn on the head of the user such as the eyewear" (hereinafter also referred to as a "fixed coordinate system corresponding to a "wearable device") may be used.

Further, the coordinate system associated with the face of the user according to the present embodiment is not limited to the fixed coordinate system corresponding to the wearable device. For example, in a case in which the position of the eye of the user is detected by one or two or more imaging devices arranged in a space such as a room in which the user stays, a coordinate system associated with the detected eye may be used. The following description will proceed with an example in which the coordinate system associated with the face of the user is the fixed coordinate system corresponding to the wearable device.

For example, the information processing apparatus according to the present embodiment specifies a plane in which the intersection points with all the set respective reference vectors are located on the plane including the display screen as the plane including the display screen according to the present embodiment.

In a case in which the display screen according to the present embodiment is the display screen of the display device, for example, a plane having the same size as the display screen (a plane corresponding to the angle of view of the display screen) or a plane specified in a region in the angle of view of the display screen and a region of an arbitrary size outside the angle of view of the display screen may be used as the plane including the display screen according to the present embodiment. Further, in a case in which the display screen according to the present embodiment is the region of the wall onto which the image is projected by the image projection device, for example, a plane having the same size as the display screen (a plane corresponding to the angle of view of the display screen) or a plane specified in a region in the angle of view of the display screen and a region of an arbitrary size outside the angle of view of the display screen may be used as the plane including the display screen according to the present embodiment. Further, in a case in which the display screen according to the present embodiment is the region of the wall onto which the image is projected by the image projection device, a plane set while ignoring an uneven portion of the wall may be used as the plane including the display screen.

For example, the information processing apparatus according to the present embodiment specifies the plane containing the display screen according to the present embodiment on the basis of a predetermined object displayed on the display screen which is detected from the captured image generated by the outward imaging device C1 (an example of a captured image obtained by imaging the forward direction of the face of the user). The information processing apparatus according to the present embodiment specifies the plane including the display screen, for example, by detecting a marker (an example of a predetermined object) from a captured image and specifying the display screen. For example, the size of the plane including the display screen is decided so that the intersection point with each of all the set reference vectors is located on the plane including the display screen as described above.

Here, the predetermined object may be, for example, an arbitrary object which can be detected from image by an arbitrary object recognition process such as the marker M illustrated in FIGS. 3A and 3B.

Figure 4:
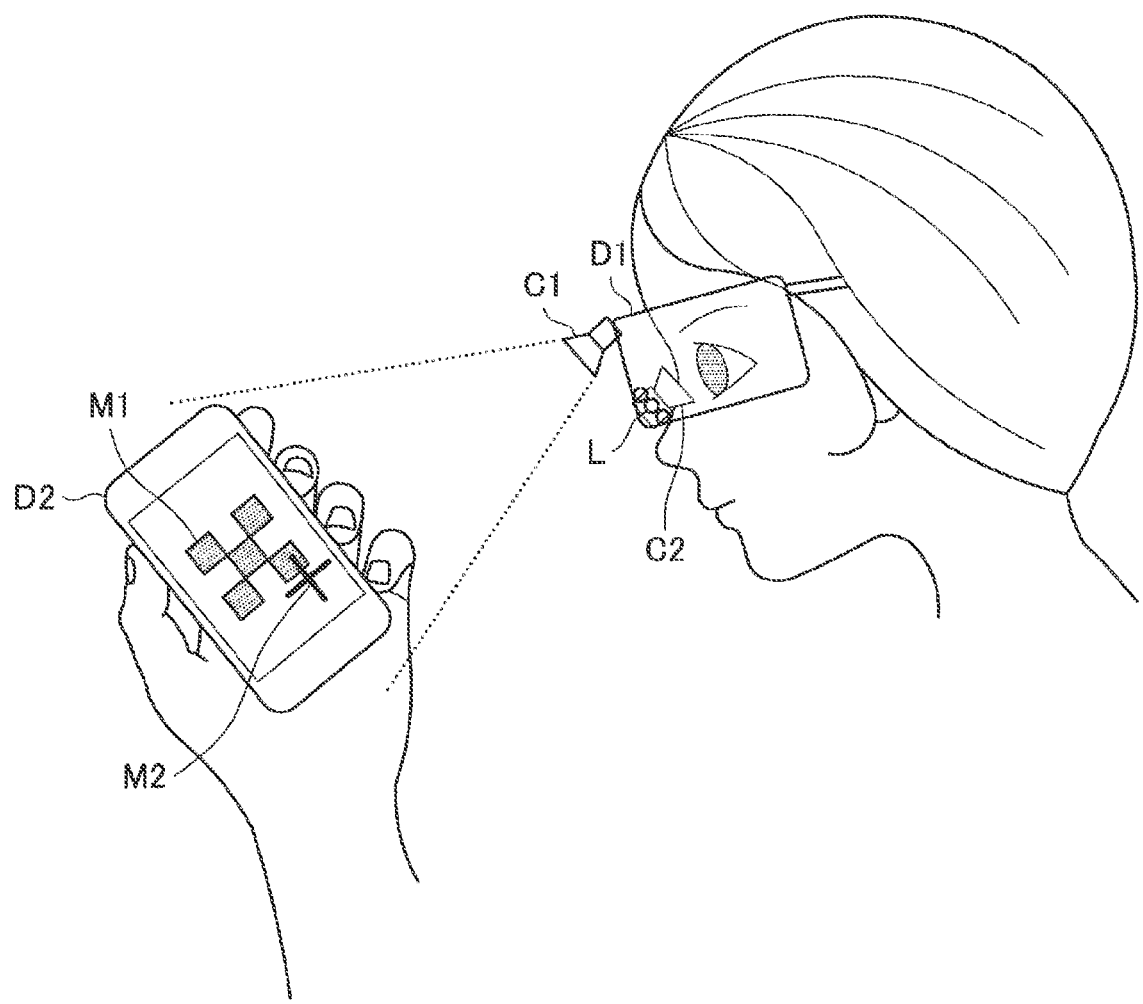
FIG. 4 is an explanatory diagram illustrating an application example of an information processing method according to the present embodiment.

FIG. 4 is an explanatory diagram illustrating an application example of the information processing method according to the present embodiment. FIG. 4 illustrates an example in which a glasses type eyewear D1 and an apparatus D2 including a display device such as a smartphone are used.

In the application example illustrated in FIG. 4, as the information processing apparatus according to the present embodiment, for example, a computer (not illustrated) such as a server may be used. In a case in which the information processing apparatus according to the present embodiment is a computer (not illustrated) such as a server, the information processing apparatus according to the present embodiment appropriately performs communication with each of the eyewear D1 and the apparatus D2 via a communication unit installed therein (to be described later) or an external communication device connected thereto.

Further, the information processing apparatus according to the present embodiment in the application example illustrated in FIG. 4 is not limited to the above example. In the application example illustrated in FIG. 4, the information processing apparatus according to the present embodiment may be the eyewear D1 or the apparatus D2. Further, the application examples of the information processing apparatus according to the present embodiment will be described later.

The eyewear D1 is a device that supports the detection of the line of sight according to the corneal reflex technique and includes, for example, the outward imaging device C1, the inward imaging device C2, and the light source L such as the IR LED.

For example, a marker M1 (an example of a predetermined object. The same applies to other drawings) for detecting the apparatus D2 (or the display screen of the apparatus D2) is displayed on the display screen of the apparatus D2.

The display of the marker M1 may be initiated by the apparatus D2 subjectively or may be performed by the information processing apparatus according to the present embodiment. The information processing apparatus according to the present embodiment causes the marker M1 to be displayed on the display screen by transmitting a control signal including a display command to, for example, a device corresponding to the display screen such as a display device or an image projection device.

Further, a marker M2 indicating the calibration position (hereinafter the same applies to other drawings) is displayed on the display screen of the apparatus D2. Here, the marker M2 is displayed on the display screen of the apparatus D2 in a case in which the intersection point of the reference vector and the plane including the display screen is located within the angle of view of the display screen of the apparatus D2.

The display of the marker M2 may be initiated by the apparatus D2 subjectively or may be performed by the information processing apparatus according to the present embodiment. The information processing apparatus according to the present embodiment causes the marker M2 to be displayed on the display screen by transmitting a control signal including a display command to, for example, a device corresponding to the display screen such as a display device or an image projection device.

As illustrated in FIG. 4, a case in which the marker M2 is displayed on the display screen corresponds to a case in which the calibration position is located on the display screen. In a case in which the marker M2 is displayed on the display screen, for example, it is possible to obtain the difference ($\Delta\varphi n$, $\Delta\theta n$) between the optical axis vector and the correct solution vector when the user is looking at the marker M2 and acquire the sampling data at the calibration position corresponding to the marker M2 being displayed.

Here, in the example illustrated in FIG. 4, the relative positional relation between the user and the display screen of the apparatus D2 may change, for example, as the user moves the position of the apparatus D2.

FIGS. 5A and 5B are explanatory diagrams for describing an example of the information processing method according to the present embodiment, and in the example illustrated in FIG. 4, the user moves the apparatus D2 to the right when seen from the user. FIG. 5A illustrates an example of a state before the user moves the apparatus D2, and FIG. 5B illustrates an example of a state after the user moves the apparatus D2. In FIGS. 5A and 5B, the reference vector corresponding to a certain calibration position is indicated by reference numeral Vo.

For example, as illustrated in FIGS. 5A and 5B, in a case in which the user moves the apparatus D2, the relative positional relation between the user and the display screen of the apparatus D2 changes. On the other hand, the reference vector Vo is a fixed vector set in the coordinate system associated with the face of the user and thus does not depend on a change in the relative positional relation between the user and the display screen of the apparatus D2.

Therefore, when the user moves the apparatus D2, the position of the intersection point of the reference vector Vo and the plane including the display screen corresponds to either of a case of (a) to be described below and a case of (b) to be described below.

(a) A case in which the position of the intersection point of the reference vector and the plane including the display screen is within the angle of view of the display screen of the apparatus D2

In a case in which the intersection point of the reference vector and the plane including the display screen is located within the angle of view of the display screen of the apparatus D2, the marker M2 is displayed at the position corresponding to the intersection point of the display screen of the apparatus D2, for example as illustrated in FIG. 5B.

Therefore, in a case in which the marker M2 is displayed on the display screen of the apparatus D2 as illustrated in FIG. 5B in the state after the user moved the apparatus D2, the information processing apparatus according to the present embodiment obtains the difference ($\Delta\varphi n, \Delta\theta n$) between the optical axis vector and the correct solution vector in a case in which the user is looking at the marker M2 and obtains the sampling data at the calibration position corresponding to the marker M2 being displayed, similarly to the example described with reference to FIG. 4.

(b) A case in which the position of the intersection point of the reference vector and the plane including the display screen is not within the angle of view of the display screen of the apparatus D2

In a case in which the intersection point of the reference vector and the plane including the display screen is not located within the angle of view of the display screen of the apparatus D2, that is, the intersection point of the reference vector and the plane including the display screen is outside the angle of view of the display screen of the apparatus D2, the calibration position is not within the angle of view of the display screen of the apparatus D2. Therefore, in the above case, the marker M2 is not displayed on the display screen of the apparatus D2.

In a case in which the calibration position is not within the angle of view of the display screen as described above, the information processing apparatus according to the present embodiment derives the relative positional relation between the user and the display screen so that the calibration position is within the angle of view of the display screen. Here, the "deriving of the relative positional relation between the user and the display screen so that the calibration position is within the angle of view of the display screen" corresponds "deriving the relative positional relation to be a positional relation in which the sampling data can be acquired."

More specifically, the information processing apparatus according to the present embodiment derives the relative positional relation between the user and the display screen so that the calibration position is within the angle of view of the display screen, for example, by performing any one of a first derivation process described in (I) to be described below to another derivation process described in (IV).

(I) First Example of Derivation Process: Visual Derivation

The information processing apparatus according to the present embodiment derives the relative positional relation between the user and the display screen by causing a derivation object for deriving the relative positional relation between the user and the display screen to be displayed on the display screen.

Here, the derivation object according to the present embodiment may be, for example, an object indicating a direction in which the user moves or a direction in which the user move the display screen. Further, the derivation object according to the present embodiment may be further displayed in an animation manner.

FIGS. 6A and 6B are explanatory diagrams for describing an example of the derivation process related to the information processing method according to the present embodiment, and illustrates a first example of the visual derivation using the derivation object. Further, FIGS. 6A and 6B illustrate an example of displaying the derivation object on the display screen of the apparatus D2 including a display device such as a smartphone. In FIGS. 6A and 6B, a reference vector corresponding to a first calibration position is indicated by reference numeral Vo1. Further, in FIGS. 6A and 6B, reference vectors corresponding to second to fifth calibration positions are indicated by reference numerals Vo2 to Vo5.

A case in which the sampling data at the calibration position corresponding to the reference vector Vo1 is acquired will be described as an example. As illustrated in FIG. 6A, in a case in which an intersection point of the reference vector Vo1 and the plane including the display screen is not located within the angle of view of the display screen of the apparatus D2, the information processing apparatus according to the present embodiment causes a derivation object M3 to be displayed on the display screen. The information processing apparatus according to the present embodiment causes the derivation object M3 to be displayed on the display screen, for example, by transmitting a control signal including a display command to the apparatus D2.

Here, the derivation object M3 illustrated in FIG. 6A is an example in which the direction of the calibration position is indicated by an arrow so that the calibration position corresponding to the reference vector Vo1 is within the angle of view of the display screen. For example, when the derivation object M3 illustrated in FIG. 6A is displayed on the display screen of the apparatus D2, for example, the user can recognize the direction of moving the display screen of the apparatus D2.

For example, if the intersection point of the reference vector Vo1 and the plane including the display screen is located within the angle of view of the display screen of the apparatus D2 by the user moving the apparatus D2 in the direction of the arrow, the marker M2 is displayed on the display screen of the apparatus D2 as illustrated in FIG. 6B. Further, the information processing apparatus according to the present embodiment obtains the difference ($\Delta\varphi n, \Delta\theta n$) between the optical axis vector and the correct solution vector when the user is looking at the marker M2 and acquires the sampling data at the calibration position corresponding to the reference vector Vo1 corresponding to the marker M2 being displayed, similarly to the example described with reference to FIG. 4.

Figure 7B:
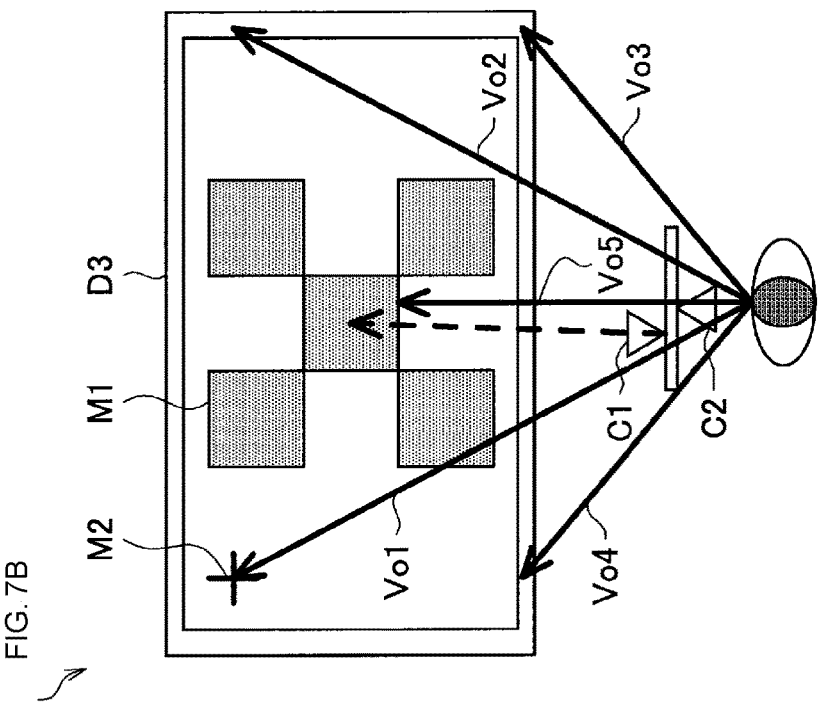
FIGS. 7A and 7B are explanatory diagrams for describing an example of a derivation process related to an information processing method according to the present embodiment.
Figure 7A:
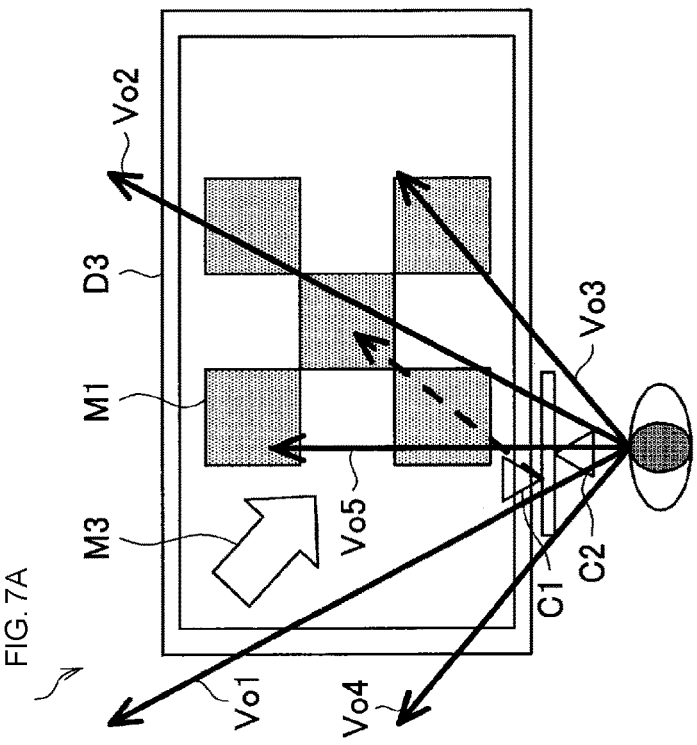

FIGS. 7A and 7B are explanatory diagrams for describing an example of the derivation process related to the information processing method according to the present embodiment, and illustrates a second example of the visual derivation using the derivation object. Further, FIGS. 7A and 7B illustrate an example of displaying the derivation object on a display screen of an apparatus D3 including a display device such as a television broadcast receiver or a monitor. In FIGS. 7A and 7B, a reference vector corresponding to a first calibration position is indicated by reference numeral Vo1. Further, in FIGS. 7A and 7B, reference vectors corresponding to second to fifth calibration positions are indicated by reference numerals Vo2 to Vo5.

A case in which the sampling data at the calibration position corresponding to the reference vector Vo1 is acquired will be described as an example. As illustrated in FIG. 7A, in a case in which an intersection point of the reference vector Vo1 and the plane including the display screen is not located within the angle of view of the display screen of the apparatus D3, the information processing apparatus according to the present embodiment causes a derivation object M3 to be displayed on the display screen. The information processing apparatus according to the present embodiment causes the derivation object M3 to be displayed on the display screen, for example, by transmitting a control signal including a display command to the apparatus D3.

Here, the derivation object M3 illustrated in FIG. 7A is an example in which the direction of the calibration position is indicated by an arrow so that the calibration position corresponding to the reference vector Vo1 is within the angle of view of the display screen. Here, the apparatus D3 is an apparatus which is difficult to move as compared with the apparatus D2. Therefore, when the derivation object M3 illustrated in FIG. 7A is displayed on the display screen of the apparatus D3, for example, the user can recognize a direction in which the user is moving.

For example, as the user moves in the direction of the arrow, the position of the reference vector Vo1 changes. Further, if the intersection point of the reference vector Vo1 and the plane including the display screen is located within the angle of view of the display screen of the apparatus D3, the marker M2 is displayed on the display screen of the apparatus D3 as illustrated in FIG. 7B. Further, the information processing apparatus according to the present embodiment obtains the difference ($\Delta\varphi n, \Delta\theta n$) between the optical axis vector and the correct solution vector when the user is looking at the marker M2 and acquires the sampling data at the calibration position corresponding to the reference vector Vo1 corresponding to the marker M2 being displayed, similarly to the example described with reference to FIG. 4.

For example, it is possible to derive the relative positional relation between the user and the display screen so that the calibration position is within the angle of view of the display screen by displaying the derivation objects M3 illustrated in FIGS. 6A, 6B, 7A, and 7B.

Further, the derivation object according to the present embodiment is not limited to the objects in which the direction illustrated in FIGS. 6A, 6B, 7A, and 7B are indicated by the arrows. For example, the derivation object according to the present embodiment may be an object indicating a character, and the character may be animated.

Figure 8A:
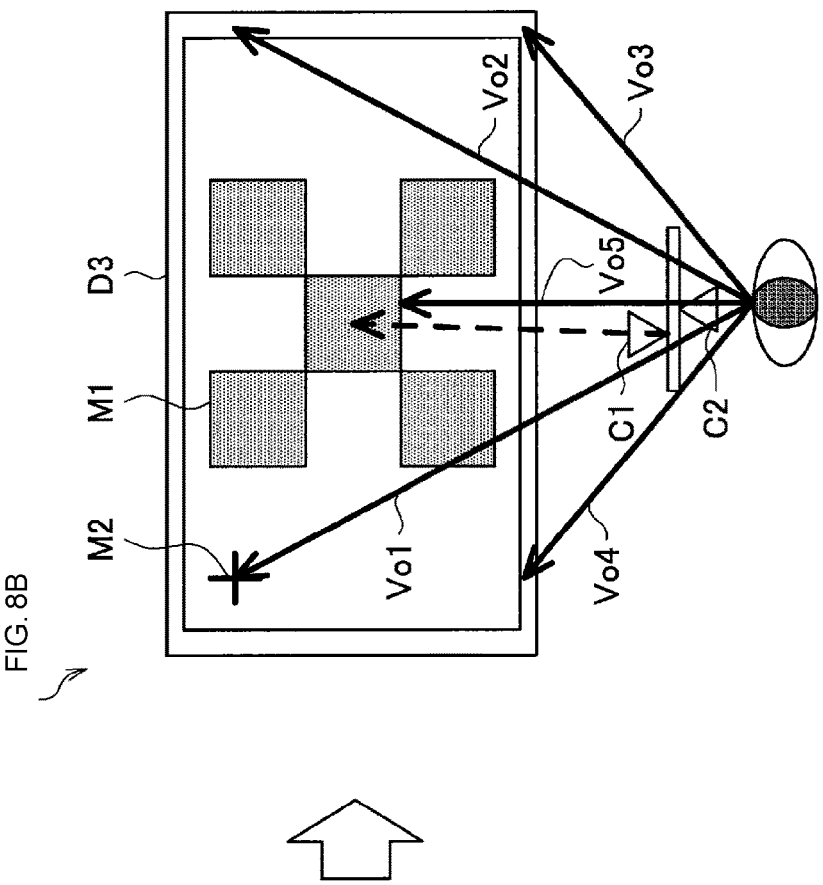
FIGS. 8A and 8B are explanatory diagrams for describing an example of a derivation process related to an information processing method according to the present embodiment.
Figure 8B:
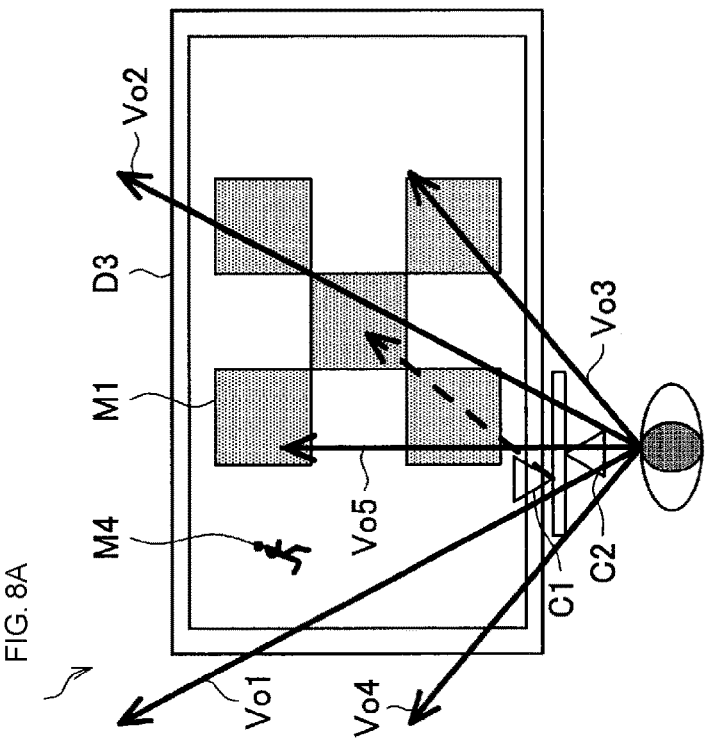

FIGS. 8A and 8B are explanatory diagrams for describing an example of the derivation process related to the information processing method according to the present embodiment, and illustrates a third example of the visual derivation using the derivation object. Further, FIGS. 8A and 8B illustrate an example of displaying the derivation object on a display screen of an apparatus D3 including a display device such as a television broadcast receiver or a monitor. In FIGS. 8A and 8B, a reference vector corresponding to a first calibration position is indicated by reference numeral Vo1. Further, in FIGS. 8A and 8B, reference vectors corresponding to second to fifth calibration positions are indicated by reference numerals Vo2 to Vo5.

A case in which the sampling data at the calibration position corresponding to the reference vector Vo1 is acquired will be described as an example. As illustrated in FIG. 8A, in a case in which an intersection point of the reference vector Vo1 and the plane including the display screen is not located within the angle of view of the display screen of the apparatus D3, the information processing apparatus according to the present embodiment causes a derivation object M4 to be displayed on the display screen. The information processing apparatus according to the present embodiment causes the derivation object M4 to be displayed on the display screen, for example, by transmitting a control signal including a display command to the apparatus D4.

Here, the derivation object M4 illustrated in FIG. 8A is an example in which a direction in which the user is moving is indicated by a character so that the calibration position corresponding to the reference vector Vo1 is within the angle of view of the display screen. Therefore, when the derivation object M4 illustrated in FIG. 8A is displayed on the display screen of the apparatus D3, for example, the user can recognize a direction in which the user is moving.

For example, as the user moves in the direction of the arrow, the position of the reference vector Vo1 changes. Further, if the intersection point of the reference vector Vo1 and the plane including the display screen is located within the angle of view of the display screen of the apparatus D3, the marker M2 is displayed on the display screen of the apparatus D3 as illustrated in FIG. 8B. Further, the information processing apparatus according to the present embodiment obtains the difference ($\Delta\varphi n, \Delta\theta n$) between the optical axis vector and the correct solution vector when the user is looking at the marker M2 and acquires the sampling data at the calibration position corresponding to the reference vector Vo1 corresponding to the marker M2 being displayed, similarly to the example described with reference to FIG. 4.

In the case in which the derivation process in accordance with the first example is carried out, for example, the information processing apparatus according to the present embodiment causes the derivation object such as the derivation object M3 illustrated in FIGS. 6A, 6B, 7A, and 7B or the derivation object M4 illustrated in FIGS. 8A and 8B to be displayed on the display screen. Thus, the information processing apparatus according to the present embodiment can derive the relative positional relation between the user and the display screen so that the calibration position is within the angle of view of the display screen.

Further, the information processing apparatus according to the present embodiment can derive the relative positional relation between the user and the display screen to be a positional relation in which the sampling data can be acquired, and thus the information processing apparatus according to the present embodiment can stably acquire the sampling data.

(II) Second Example of Derivation Process: Visual Derivation

The information processing apparatus according to the present embodiment derives the relative positional relation between the user and the display screen by causing a sound for deriving the relative positional relation between the user and the display screen to be output from an audio output device such as a speaker.

The sound for deriving the relative positional relation between the user and the display screen may be, for example, a sound indicating a direction in which the user moves or a direction in which an apparatus corresponding to the display screen is moved. The information processing apparatus according to the present embodiment causes the sound such as the sound for deriving to be output from the audio output device, for example, by transmitting a control signal including audio data and an audio output command to the audio output device or a device including the audio output device.

In a case in which the derivation process according to the second example is carried out, for example, the information processing apparatus according to the present embodiment causes the sound for deriving the relative positional relation between the user and the display screen such as the sound indicating the direction in which the user moves or the direction in which the apparatus corresponding to the display screen is moved to be output from the audio output device. Thus, the information processing apparatus according to the present embodiment can derive the relative positional relation between the user and the display screen so that the calibration position is within the angle of view of the display screen.

Further, the information processing apparatus according to the present embodiment can derive the relative positional relation between the user and the display screen to be a positional relation in which the sampling data can be acquired, and thus the information processing apparatus according to the present embodiment can stably acquire the sampling data.

(III) Third Example of Derivation Process

The information processing apparatus according to the present embodiment can perform visual and auditory derivation by performing a process in which the derivation process according to the first example described in (I) and the derivation process according to the second example described in (II) are combined.

(IV) Other Examples of Derivation Process

Further, the derivation process according to the present embodiment is not limited to the derivation process according to the first example described in (I) to the derivation process according to the third example described in (III). For example, the information processing apparatus according to the present embodiment can further perform one or more of processes described in (IV-1) to (IV-3) to be described below in any one of the derivation process according to the first example described in (I) to the derivation process according to the third example described in (III).

(IV-1)

The information processing apparatus according to the present embodiment can also notify the user of an derived state. The information processing apparatus according to the present embodiment can notify the user of the derived state of the user through one or more of, for example, a visual method, an auditory method, and a haptic method.

As the notification of the derived state using the visual method, for example, the notification indicating that the derivation is being performed may be given by causing an image indicating that the derivation is being performed to be displayed on the display screen, causing a light emitting device (a light emitting diode (LED) or the like) that indicates that the derivation is being performed by light emission to emit light, or the like.

Further, the notification of the derived state using the visual method is not limited to the above examples. For example, as another example of the notification of the derived state using the visual method, an "image indicating a positional relation between the calibration position which is a target of derivation and a current position of the display screen" (for example, an image in which the positional relation is indicated in the form of a map or the like) may be displayed on a region of a part of the display screen or a display screen of another display device different from the display screen. Further, the derived state may be visually notified of by indicating a degree of progress of derivation using a numerical value or the like.

Further, as the notification of the derived state using the auditory method, for example, a sound indicating that the derivation is being performed may be output from an audio output device such as a speaker. Further, the notification of the derived state using the auditory method is not limited to the above example. For example, as another example of notification of the derived state using the auditory method, a sound indicating the degree of progress of derivation may be output from the audio output device.

Further, as the notification of the derived state using the haptical method, for example, a notification indicating that the derivation is being performed may be given through vibration feedback given by causing a vibration device to vibrate. Further, the notification of the derived state using the haptic method is not limited to the above example. For example, as another example of the notification of the derived state using the haptical method, the degree of progress of derivation may be notified of using a vibration strength (for example, vibration feedback of increasing the vibration as the calibration position is closer to within the angle of view of the display screen.

For example, since the derived state is notified of as described above, the user can recognize, for example, that the derivation is being conducted, the progress of the derivation, and the like. Further, it will be appreciated that the example of the notification of the derived state is not limited to the above examples.

(IV-2)

The information processing apparatus according to the present embodiment may perform the derivation process in a case in which a set start condition is determined to be satisfied.

Here, as a case in which the start condition according to the present embodiment is determined to be satisfied, for example, there is a case in which one or more of the following cases are satisfied:

a case in which the calibration information is not stored in a recording medium (for example, an initial state);

a case in which a set period elapses after the last calibration information is generated;

a case in which a predetermined manipulation such as a manipulation of performing calibration is detected;

a case in which a set user is detected as a result of arbitrary biometric authentication such as face recognition based on a captured image; and a case in which it is determined that the calibration is necessary on the basis of an execution result of software using the line of sight (IV-3)

The information processing apparatus according to the present embodiment can also cause a game for calibrating the line of sight (an example of application software. Hereinafter referred to simply as a "game") to be executed in a case in which the calibration of the line of sight is performed and perform the derivation process as a process of the game.

FIGS. 9A, 9B, 9C, and 9D are explanatory diagrams for describing an example of the derivation process related to the information processing method according to the present embodiment, and illustrates an example of derivation using a game for calibrating the line of sight. FIGS. 9A, 9B, 9C, and 9D illustrate an example of content displayed on the display screen of the apparatus including the display device such as a smartphone in a case in which derivation using a game for calibrating the line of sight is performed.

FIGS. 9A, 9B, 9C, and 9D illustrate an example of deriving the relative positional relation between the user and the display screen by causing a rendering position of an arbitrary object capable of attracting attention of the user such as a person, an animal, a car, or an airplane to be moved. Hereinafter, an object related to the game such as the person or the animal is referred to as a "game object" for the sake of convenience. Here, the game object corresponds to an example of the derivation object for deriving the relative positional relation between the user and the display screen.

Further, in FIGS. 9A, 9B, 9C, and 9D, a "game of causing the user to track the game object O indicating a person displayed on the display screen with the line of sight" is illustrated as an example of the game for calibrating the line of sight. In the game illustrated in FIGS. 9A, 9B, 9C, and 9D, the sampling data is acquired by tracking the game object O indicating the person with the line of sight of the user.

The game illustrated in FIGS. 9A, 9B, 9C, and 9D is performed, for example, in the flow described in (i) to (iv) to be described below.

(i) FIG. 9A

For example, if the game is started on the basis of a manipulation of the user or automatically, an image indicating content of the game is displayed on the display screen as illustrated in FIG. 9A. Here, as a case in which the game is automatically started, for example, there is a case in which the start condition is determined to be satisfied.

(ii) FIG. 9B

If the game is started, movement of the game object O indicating the person is started. Here, the game object O moves within the angle of view of the display screen so that the game object O passes through a position at which the calibration is desired to be performed. The movement of the game object O within the angle of view is implemented by changing the rendering position on the display screen. In FIG. 9B, positions indicated by reference numerals P1 to P6 correspond to examples of the positions at which the calibration is desired to be performed.

Further, in a case in which the position at which the calibration is desired to be performed is outside the angle of view of the display screen, the game object O moves toward the position at which the calibration is desired to be performed outside the angle of view. Further, if the rendering position of the game object O is no longer within the angle of view of the display screen, the game object O is not displayed on the display screen.

Further, a trajectory of the movement of the game object O illustrated in FIG. 9B may be displayed on the display screen or may not be displayed on the display screen.

(iii) FIG. 9C

For example, in a case in which the game object O moves in a lower right direction of the display screen and is not displayed on the display screen as illustrated in FIG. 9B, the user can visually recognize a direction in which the game object O is located outside the angle of view of the display screen. Further, if the user moves the apparatus including the display device such as a smartphone from a state of FIG. 9B in the lower right direction of the display screen on the basis of the recognition result, the game object O is displayed again on the display screen as illustrated in FIG. 9C.

Therefore, with the movement of the game object O, the derivation of "the relative positional relation between the user and the display screen so that the position P 6 at which the calibration is desired to be performed outside the angle of view of the display screen at the time point of FIG. 9B is within the angle of view of the display screen" is implemented.

(iv) FIG. 9D

Further, even in a case in which the game object O moves in an arbitrary direction from the state of FIG. 9C, it is possible to derive the relative positional relation between the user and the display screen, similarly to the example illustrated in FIG. 9B or FIG. 9C. FIG. 9D illustrates an example in which the game object O moves in an upper left direction of the display screen in the state FIG. 9C.

For example, the game illustrated in FIGS. 9A, 9B, 9C, and 9D is performed, for example, until acquisition of the sampling data is completed at each position at which the calibration is desired to be performed.

In a case in which the game for calibrating the line of sight as illustrated in FIGS. 9A, 9B, 9C, and 9D is used, the sampling data is acquired by the user performing the game. Therefore, in a case in which the game illustrated in FIGS. 9A, 9B, 9C, and 9D is used, it is possible to acquire the sampling data while the user is enjoying the game, for example, and thus it is possible to further reduce the load of the user related to the acquisition of the sampling data.

Further, in a case in which the game for calibrating the line of sight illustrated in FIGS. 9A, 9B, 9C, and 9D is used, an incentive for causing the user to play the game may be given to the user. As the incentive for causing the user to play the game, for example, points that can be used for various services can be given.

Further, the game for calibrating the line of sight according to the present embodiment is not limited to the example illustrated in FIGS. 9A, 9B, 9C, and 9D.

For example, the game for calibrating the line of sight according to the present embodiment may be an arbitrary game that can prompt the movement of the apparatus including the display device such as a smartphone.

Further, the game for calibrating the line of sight according to the present embodiment may be, for example, an arbitrary game capable of prompting the user to move the position. For example, the game capable of prompting the user to move the position is applied to the apparatus including the display device such as a television broadcast receiver, a monitor, or the like such as the apparatus D3 illustrated in FIGS. 7A and 7B.

As described above, the information processing apparatus according to the present embodiment performs the "derivation process of deriving the relative positional relation between the user of the line of sight detection target and the display screen so that the calibration position is within the angle of view of the display screen" as the process related to the information processing method according to the present embodiment.

In this regard, with the derivation process, it is possible to easily cause the calibration position based on the reference vector corresponding to the forward direction of the face of the user to be within the angle of view of the display screen.

Therefore, when the derivation process is performed, the sampling data for the calibration of the line of sight can be acquired at an arbitrary calibration position based on the reference vector.

Further, even in a case in which the calibration position is outside the angle of view of the display screen, when the derivation process is performed, it is possible to acquire the sampling data for the calibration of the line of sight.

Further, when the derivation process is performed, even in a case in which the wearable device worn on the head of the user not equipped with the display device such as the eyewear not equipped with the display device is used, it is possible to acquire the sampling data for the calibration of the line of sight.

Therefore, as the derivation process is performed as the process related to the information processing method in accordance with the embodiment, it is possible to improve the stability of the acquisition of the sampling data for the calibration of the line of sight.

Further, since the stability of the acquisition of the sampling data can be improved, it is possible to stably use the line of sight of the user with the accuracy which is originally intended.

[3-2] Other Processes Related to Information Processing Method According to Present Embodiment Further, the process related to the information processing method according to the present embodiment is not limited to the processes described above. Other processes related to the information processing method according to the present embodiment will be described below. The information processing apparatus according to the present embodiment can further perform, for example, one or more of processes described in (1) to (3) to be described below as the process related to the information processing method according to the present embodiment.

(1) Calibration Process

The information processing apparatus according to the present embodiment performs a calibration process of calibrating the detection result of the line of sight on the basis of the calibration information based on the acquired sampling data. The information processing apparatus according to the present embodiment calibrates the detection result of the line of sight, for example, by performing the process related to the method of calibrating the detection result of the line of sight described above.

Here, the calibration information may be generated by the information processing apparatus according to the present embodiment or may be generated in the external apparatus of the information processing apparatus according to the present embodiment. In a case in which the information processing apparatus according to the present embodiment generates the calibration information, the information processing apparatus according to the present embodiment calibrates the detection result of the line of sight on the basis of the generated calibration information. Further, in a case in which the calibration information is generated in the external apparatus, the information processing apparatus according to the present embodiment acquires the calibration information transmitted from the external apparatus via communication through a communication unit installed therein (to be described later) or an external communication device connected thereto and calibrates the detection result of the line of sight on the basis of the acquired calibration information.

As described above, the derivation process according to the present embodiment is performed, and thus the acquisition of the sampling data is stabilized. Therefore, the information processing apparatus according to the present embodiment can perform the calibration with a high degree of accuracy by calibrating the detection result of the line of sight on the basis of the calibration information based on the sampling data acquired by performing the derivation process according to the present embodiment.

(2) Stare Detection Process

The information processing apparatus according to the present embodiment acquires information related to a stare on the basis of the calibrated detection result of the line of sight.

As the calibrated detection result of the line of sight according to the present embodiment, for example, information indicating the visual axis estimated on the basis of the optical axis (for example, data indicating the visual axis vector or the like) may be used.

As the information related to the stare according to the present embodiment, data indicating one or both of an estimated stare direction and an estimated stare position may be used. The stare direction according to the present embodiment may be, for example, a central direction perceived by the user, and the stare position according to the present embodiment may be, for example, a position perceived by the user.

The information processing apparatus according to the present embodiment obtains the stare direction by estimating the direction of the line of sight, for example, on the basis of the calibrated detection result of the line of sight. Further, the information processing apparatus according to the present embodiment obtains the stare position by estimating the position of the line of sight, for example, on the basis of the calibrated detection result of the line of sight.

(3) Software Control Process

The information processing apparatus according to the present embodiment performs, for example, a process of controlling software that uses the information related to the stare. Here, examples of the software that uses the information related to the stare include an operating system (OS), system software, and application software.

For example, the information processing apparatus according to the present embodiment causes software to perform an operation corresponding to either or both of the stare direction and the stare position indicated by the information related to the stare. Here, the software controlled by the information processing apparatus according to the present embodiment may be software which is executed in the information processing apparatus according to the present embodiment or may be software which is executed in the external apparatus of the information processing apparatus according to the present embodiment. In a case in which the software controlled by the information processing apparatus according to the present embodiment is the software executed in the external apparatus, the information processing apparatus according to the present embodiment controls the software by transmitting a control signal including a control command for controlling software to the external apparatus.

Here, the information related to the stare used in the software control process may be information obtained by the process of (2) (the stare detection process) or may be information obtained by from the external apparatus via communication with the external apparatus via a communication unit (to be described later) or the like installed in the external apparatus.

Figure 10:
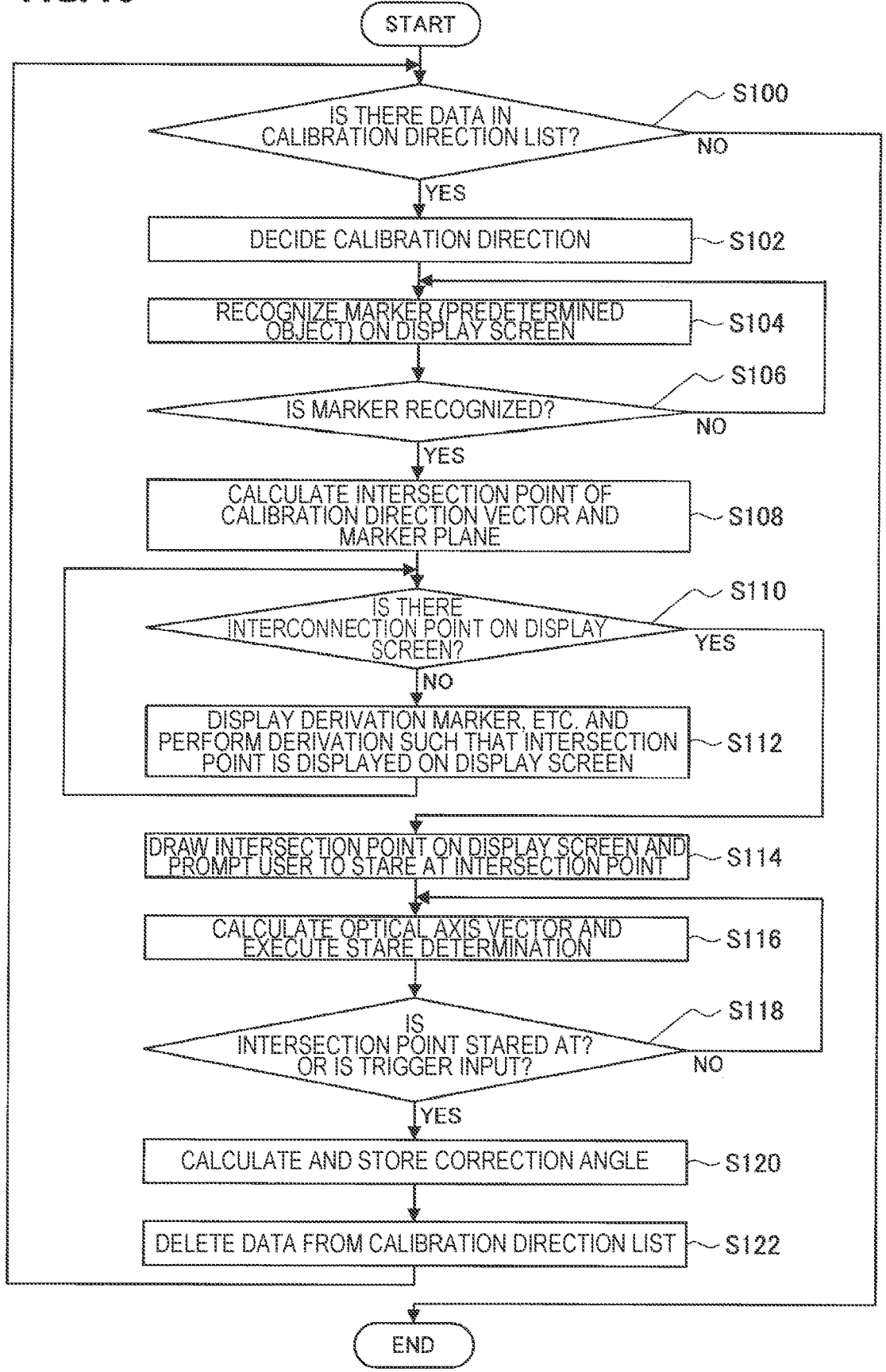
FIG. 10 is a flowchart illustrating an example of a process related to the information processing method according to the embodiment.

[3-3] Example of Process Related to Information Processing Method According to Present Embodiment Next, an example of the process related to the information processing method according to the present embodiment will be described. FIG. 10 is a flowchart illustrating an example of the process related to the information processing method according to the present embodiment. Here, FIG. 10 illustrates an example of a process in a case in which the sampling data is acquired by the derivation process as an example of the process related to the information processing method according to the present embodiment.

The information processing apparatus according to the present embodiment determines whether or not there is unprocessed data in a calibration direction list (S100). Here, the calibration direction indicated by the calibration direction list corresponds to the direction corresponding to the reference vector.

In a case in which it is determined that there is no unprocessed data in step S100, the information processing apparatus according to the present embodiment ends the process illustrated in FIG. 10. Here, a case in which it is determined that there is no unprocessed data in step S100 corresponds to a case in which the process for all the calibration directions is completed.

Further, in a case in which it is determined that there is unprocessed data in step S100, the information processing apparatus according to the present embodiment decides the calibration direction (S102).

The information processing apparatus according to the present embodiment recognizes the marker (an example of a predetermined object) on the display screen (S104). For example, the information processing apparatus according to the present embodiment recognizes the marker (an example of a predetermined object) on the display screen on the basis of the captured image captured by the outward imaging device C1.

The information processing apparatus according to the present embodiment determines whether or not the marker (an example of a predetermined object) on the display screen is recognized (S106).

In a case in which it is determined in step S106 that the marker (an example of a predetermined object) on the display screen is not recognized, the information processing apparatus according to the present embodiment repeats the process from step S104.

Further, in a case in which it is determined in step S106 that the marker (an example of a predetermined object) on the display screen is recognized, the information processing apparatus according to the present embodiment calculates an intersection point of a calibration direction vector (the reference vector) and a marker plane (the plane including the display screen) (S108).

The information processing apparatus according to the present embodiment determines whether or not there is the intersection point obtained in step S108 on the display screen (S110). The information processing apparatus according to the present embodiment determines that there is the intersection point on the display screen in a case in which the intersection point is located within the angle of view of the display screen.

In a case in which it is determined in step S110 that there is no intersection point on the display screen, the information processing apparatus according to the present embodiment derives the intersection point to be displayed on the display screen by causing a derivation marker (an example of the derivation object) or the like to be displayed on the display screen (S112). Further, as described above, the information processing apparatus according to the present embodiment may derive the intersection point to be displayed on the display screen by outputting a voice for deriving or the like.

If the process of step S112 is performed, the information processing apparatus according to the present embodiment repeats the process from step S110.

Further, in a case in which it is determined in step S110 that there is the intersection point on the display screen, the information processing apparatus according to the present embodiment causes the intersection point to be drawn on the display screen and prompts the user to stare at the intersection point (S114). For example, the information processing apparatus according to the present embodiment causes the intersection point to be drawn on the display screen by causing an object indicating the calibration position to be displayed on the display screen.

The information processing apparatus according to the present embodiment calculates the optical axis vector (an example of the detection result of the line of sight) and determines whether or not the intersection point drawn on the display screen is stared at (S116).

The information processing apparatus according to the present embodiment determines whether it is determined that the intersection point drawn on the display screen is stared at or whether a predetermined trigger is detected (S118). For example, in a case in which the intersection point of the optical axis vector and the display screen is included in a predetermined region including the intersection point drawn on the display screen, the information processing apparatus according to the present embodiment determines that the intersection point drawn on the display screen is stared at. Further, for example, in a case in which a predetermined manipulation such as a manipulation of pressing a button for starting the acquisition of the sampling data is detected, the information processing apparatus according to the present embodiment determines that the predetermined trigger is detected. Further, it will be appreciated that the example of the process of step S118 is not limited to the above example.

In a case in which it is determined in step S118 that the intersection point drawn on the display screen is not stared at or that a predetermined trigger is not detected, the information processing apparatus according to the present embodiment repeats the process from step S116.

Further, in a case in which it is determined in step S118 that the intersection point drawn on the display screen is stared at or that a predetermined trigger is detected, the information processing apparatus according to the present embodiment calculates a correction angle, and causes the correction angle to be recorded in a recording medium (S120). Here, the correction angle corresponds to an example of the sampling data corresponding to the difference between the optical axis vector and the correct solution vector.

Upon completion of the process of step S120, the information processing apparatus according to the present embodiment deletes the processed data from the calibration direction list (S122). Then, the information processing apparatus according to the present embodiment repeats the process from step S100.

The information processing apparatus according to the present embodiment performs, for example, the process illustrated in FIG. 10 as the process related to the information processing method according to the present embodiment. Further, the example of the process related to the information processing method according to the present embodiment is not limited to the example illustrated in FIG. 10.

For example, in either or both of the case in which the process of step S120 is completed (in a case in which the process for one calibration direction is completed) and the case in which it is determined that there is no unprocessed data in step S100 (in a case in which the process for all the calibration directions is completed), the information processing apparatus according to the present embodiment may give a notification indicating that the process is completed. For example, the information processing apparatus according to the present embodiment gives the notification indicating that the process is completed to the user using either or both of a visual notification method of causing a character, an image, or the like to be displayed on the display screen and an auditory notification method using a sound.

(Information Processing Apparatus According to Embodiment)

Next, an example of a configuration of the information processing apparatus according to the embodiment capable of performing the process related to the information processing method according to the embodiment described above will be described.

Figure 11:
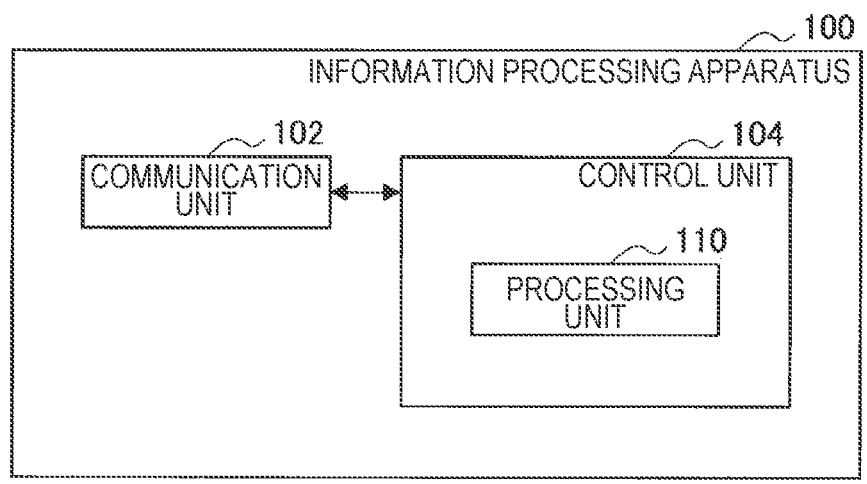
FIG. 11 is a block diagram illustrating an example of a configuration of an information processing apparatus according to the embodiment.

FIG. 11 is a block diagram illustrating an example of a configuration of an information processing apparatus 100 according to the embodiment. The information processing apparatus 100 includes, for example, a communication unit 102 and a control unit 104.

Moreover, for example, the information processing apparatus 100 may include, a read-only memory (ROM which is not illustrated), a random access memory (RAM which is not illustrated), a storage unit (not illustrated), a manipulation unit (not illustrated) which can be manipulated by a user of the information processing apparatus 100, and a display unit (not illustrated) that displays various screens on a display screen. In the information processing apparatus 100, for example, the constituent elements are connected via a bus serving as a data transmission path.

The ROM (not illustrated) stores a program or control data such as calculation parameters which are used by the control unit 104. The RAM (not illustrated) temporarily stores a program or the like which is executed by the control unit 104.

A storage unit (not illustrated) is a storage unit installed in the information processing apparatus 100, and stores, for example, data related to the information processing method according to the present embodiment such as data indicating the reference vector such as the calibration direction list, the sampling data, the calibration information, or a database used for an object recognition process of recognizing a predetermined object or the like from the captured image, and various data such as various applications. Here, as the storage unit (not illustrated), for example, a magnetic recording medium such as a hard disk and a nonvolatile memory such as a flash memory can be exemplified. Moreover, the storage unit (not illustrated) may be detachably mounted on the information processing apparatus 100.

As the manipulation unit (not illustrated), a manipulation input device to be described below can be exemplified. Moreover, as the display unit (not illustrated), a display device to be described below can be exemplified.

[Example of Hardware Configuration of Information Processing Apparatus 100]

Figure 12:
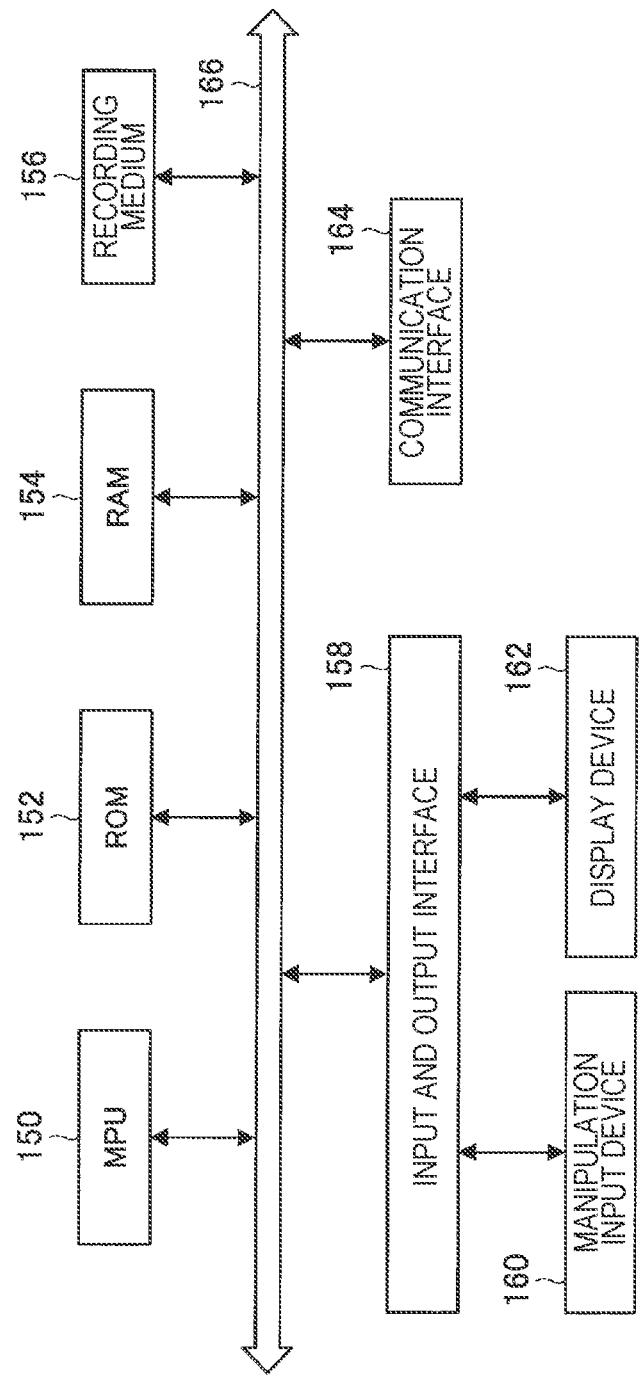
FIG. 12 is an explanatory diagram illustrating an example of a hardware configuration of the information processing apparatus according to the embodiment.

FIG. 12 is an explanatory diagram illustrating an example of a hardware configuration of the information processing apparatus 100 according to the embodiment. The information processing apparatus 100 includes, for example, an MPU 150, a ROM 152, a RAM 154, a recording medium 156, an input and output interface 158, a manipulation input device 160, a display device 162, and a communication interface 164. Moreover, in the information processing apparatus 100, for example, the constituent elements are connected via a bus 166 serving as a data transmission path. Further, the information processing apparatus 100 is driven by, for example, electric power supplied from an internal power source such as a battery installed in the information processing apparatus 100, electric power supplied from a connected external power source, or the like.

For example, the MPU 150 includes one or two or more processors or various processing circuits including a calculation circuit such as a micro processing unit (MPU), and functions as the control unit 104 controlling the entire information processing apparatus 100. Moreover, the MPU 150 plays roles of, for example, a processing unit 110 to be described below in the information processing apparatus 100. Note that the processing unit 110 may include a dedicated (or general-purpose) circuit (for example, a processor different from the MPU 150) capable of realizing a process of the processing unit 110.

The ROM 152 stores a program or control data such as calculation parameters which is used by the MPU 150. For example, the RAM 154 temporarily stores a program or the like which is executed by the MPU 150.

The recording medium 156 functions as a storage unit (not illustrated) and stores, for example, data related to the information processing method according to the embodiment, such as the sampling data or the calibration information and various kinds of data such as various applications. Here, as the recording medium 156, for example, a magnetic recording medium such as a hard disk and a nonvolatile memory such as a flash memory can be exemplified. Moreover, the recording medium 156 may be detachably mounted on the information processing apparatus 100.

The input and output interface 158 connects, for example, the manipulation input device 160 or the display device 162. The manipulation input device 160 functions as a manipulation unit (not illustrated) and the display device 162 functions as a display unit (not illustrated). Here, as the input and output interface 158, for example, a Universal Serial Bus (USB) terminal, a Digital Visual Interface (DVI) terminal, a High-Definition Multimedia Interface (HDMI) (registered trademark) terminal, and various processing circuits can be exemplified.

Moreover, for example, the manipulation input device 160 can be installed on the information processing apparatus 100 and is connected to the input and output interface 158 inside the information processing apparatus 100. As the manipulation input device 160, for example, a button, an arrow key, a rotary selector such as a jog dial, or a combination thereof can be exemplified.

Moreover, for example, the display device 162 can be installed on the information processing apparatus 100 and is connected to the input and output interface 158 inside the information processing apparatus 100. As the display device 162, for example, a liquid crystal display or an organic electro-luminescence display (or also referred to as an organic light emitting diode display) can be exemplified.

In addition, it is regardless to say that the input and output interface 158 can be connected to an external device such as an external manipulation input device (for example, a keyboard or a mouse) or an external display device of the information processing apparatus 100. Moreover, the display device 162 may be, for example, a device in which display and a user manipulation are possible, such as a touch panel.

The communication interface 164 is communication means included in the information processing apparatus 100 and functions as the communication unit 102 that performs wireless or wired communication with an external apparatus or an external device. Here, as the communication interface 164, for example, a communication antenna and a radio frequency (RF) circuit (for wireless communication), an IEEE 802.15.1 port and a transmission and reception circuit (for wireless communication), an IEEE 802.11 port and a transmission and reception circuit (for wireless communication), or a Local Area Network (LAN) terminal and a transmission and reception circuit (for wired communication) can be exemplified.

The information processing apparatus 100 that has, for example, the configuration illustrated in FIG. 12 performs the process related to the information processing method according to the embodiment. In addition, a hardware configuration of the information processing apparatus 100 according to the embodiment is not limited to the configuration illustrated in FIG. 12.

For example, the information processing apparatus 100 does not have to include the communication interface 164 in a case in which communication with an external apparatus is performed via a connected external communication device. Moreover, the communication interface 164 may be capable of performing communication with one or two or more external apparatuses in conformity with a plurality of communication schemes.

Moreover, for example, the information processing apparatus 100 does not have to include the recording medium 156, the manipulation input device 160, or the display device 162.

Further, the information processing apparatus 100 can employ, for example, a configuration according to an application example of the information processing apparatus 100 to be described later.

Moreover, a part or the whole of the structural elements illustrated in FIG. 12 (or a configuration according to a modification example) may be realized by one or two or more integrated circuits (ICs).

Referring back to FIG. 11, an example of the configuration of the information processing apparatus 100 will be described. The communication unit 102 is communication means included in the information processing apparatus 100 and performs wireless or wired communication with an external apparatus via a network (or directly). Moreover, the communication of the communication unit 102 is controlled by, for example, the control unit 104.

Here, as the communication unit 102, for example, a communication antenna and an RF circuit or a LAN terminal and a transmission and reception circuit can be exemplified. However, the configuration of the communication unit 102 is not limited to the foregoing configuration. For example, the communication unit 102 can have a configuration corresponding to any standard capable of performing communication, such as a USB terminal and a transmission and reception circuit or have any configuration capable of communicating an external apparatus via a network. Moreover, the communication unit 102 may have a configuration capable of performing communication with one or two or more external apparatuses in conformity with a plurality of communication schemes.

The control unit 104 is implemented by, for example, an MPU and plays a role in controlling the entire information processing apparatus 100. Moreover, the control unit 104 includes, for example, a processing unit 110 and plays a role in leading the process related to the information processing method according to the embodiment.

The processing unit 110 plays a leading role of performing the process related to the information processing method according to the present embodiment.

The processing unit 110 performs the "derivation process of deriving the relative positional relation between the user and the display screen so that the calibration position is within the angle of view of the display screen." For example, in a case in which the calibration position is not within the angle of view of the display screen, the processing unit 110 derives the relative positional relation so that the calibration position is within the angle of view of the display screen.

Further, for example, the processing unit 110 may further perform one or more of the processes (the calibration process) described in (1) to the process) (the software control process) described in (3.

Further, for example, the processing unit 110 can also perform various processes related to the information processing method according to the present embodiment such as the object recognition process of recognizing a predetermined object from an image or the like, a process related to display control in an external display device, or the like.

Figure 13:
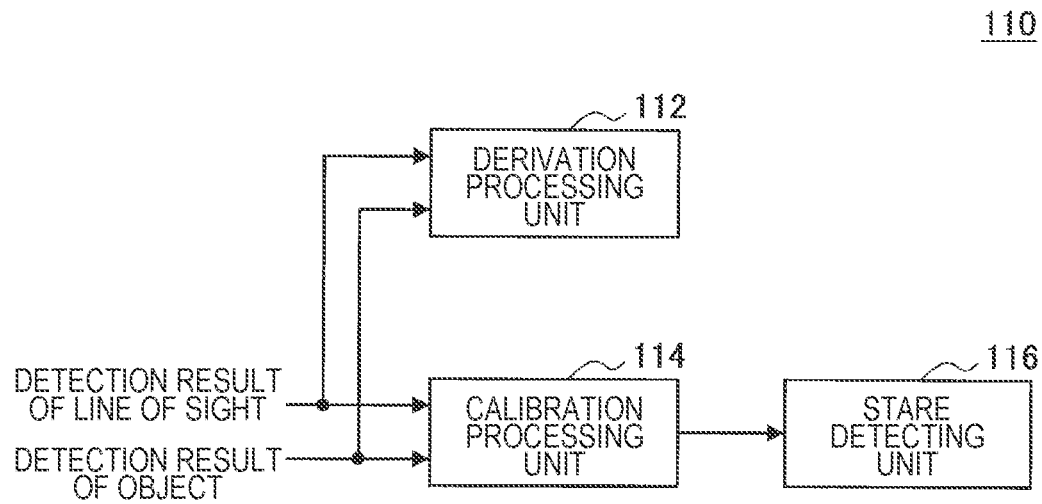
FIG. 13 is a block diagram for describing an example of a function of a processing unit of an information processing apparatus according to the present embodiment.

FIG. 13 is a block diagram for describing an example of the function provided by the processing unit 110 installed in the information processing apparatus 100 according to the present embodiment. FIG. 13 illustrates an example of a configuration in a case in which the processing unit 110 has a function of further performing the process (the calibration process) described in (1) and the process (the stare detection process) described in (2). Here, for example, the detection result of the object illustrated in FIG. 13 corresponds to a detection result (recognition result) of a predetermined object based on the captured image captured by the outward imaging device C1 or the like. The process related to the detection of a predetermined object may be performed by the information processing apparatus 100 (for example, the processing unit 110) or may be performed in the external apparatus of the information processing apparatus 100.

The processing unit 110 includes, for example, a derivation processing unit 112, a calibration processing unit 114, and a stare detecting unit 116.

The derivation processing unit 112 performs the derivation process according to the present embodiment. For example, in a case in which the calibration position is not within the angle of view of the display screen, the derivation processing unit 112 derives the relative positional relation between the user and the display screen such that the calibration position is within the angle of view of the display screen.

The calibration processing unit 114 performs the process (1) (the calibration process).

For example, the calibration processing unit 114 generates the calibration information on the basis of the sampling data. Then, the calibration processing unit 114 associates the generated calibration information with information indicating user (for example, one or more pieces of data capable of identifying the user such as a user ID or biometric information of the user) and causes the associated information to be recorded in a recording medium such as the storage unit (not illustrated) or an external recording medium.

Here, the process of generating the calibration information is performed, for example, in a case in which the calibration information is not stored in the recording medium (for example, the initial state), in a case in which a set period elapses after the last calibration information is generated, or in a case in which a manipulation for performing the calibration is detected.

Further, for example, the calibration processing unit 114 calibrates the detection result of the line of sight on the basis of the calibration information.

On the basis of the calibrated detection result of the line of sight, the stare detecting unit 116 acquires the information related to the stare corresponding to the user. The stare detecting unit 116 acquires the information related to the stare by estimating one or both of the stare direction and the stare position on the basis of the calibrated detection result of the line of sight.

For example, with the configuration illustrated in FIG. 13, the processing unit 110 plays a leading role of performing the process related to the information processing method according to the present embodiment. Further, the configuration of the processing unit 110 is not limited to the example illustrated in FIG. 13. For example, the processing unit 110 may further have a function of performing the process (the software control process) described in (3). Further, for example, the processing unit 110 may be configured not to include one or both of the calibration processing unit 114 and the stare detecting unit 116 illustrated in FIG. 13.

For example, with the configuration illustrated in FIG. 11, the information processing apparatus 100 performs the process related to the information processing method according to the present embodiment. Therefore, for example, with the configuration illustrated in FIG. 11, the information processing apparatus 100 can improve the stability of the acquisition of the sampling data for the calibration of the line of sight.

Further, for example, with the configuration illustrated in FIG. 11, the information processing apparatus 100 can obtain the effect obtained by performing the process related to the information processing method according to the present embodiment described above.

Further, the configuration of the information processing apparatus according to the present embodiment is not limited to the configuration illustrated in FIG. 11.

For example, the information processing apparatus according to the present embodiment can include the processing unit 110 illustrated in FIG. 11 separately from the control unit 104 (for example, can have an implementation by another processing circuit). Further, the processing unit 110 may be implemented by a plurality of processing circuits, and each function may be distributed to and performed by a plurality of processing circuits.

Further, the configuration for implementing the process related to the information processing method according to the present embodiment is not limited to the configuration illustrated in FIG. 11, and a configuration corresponding to the method of dividing the process related to the information processing method according to the present embodiment may be employed.

Further, for example, in a case in which communication with the external apparatus is performed via the external communication device having a similar function and configuration to the communication unit 102, the information processing apparatus according to the present embodiment may not include the communication unit 102.

The present embodiment has been described in connection with an information processing apparatus, but the present embodiment is not limited to such a form. The present embodiment can be applied to various devices which are capable of performing the process related to the information processing method according to the present embodiment such as, for example, "computers such as personal computers (PCs) or servers," "any wearable apparatuses which can be worn on the body of the user and used such as an apparatus worn on the head of the user such as an eyewear type, clock type apparatuses, or wristband type apparatuses," "communication apparatuses such as smartphones," "image projection apparatuses such as projectors," "display apparatuses," "tablet type apparatuses," "game machines," or "mobile objects such as automobiles." Further, for example, the present embodiment can also be applied to processing ICs which can be incorporated into the above-mentioned devices.

Further, the information processing apparatus according to the present embodiment may be applied to a processing system based on a connection to a network (or communication between apparatuses) such as cloud computing or the like. An example of the processing system in which the process related to the information processing method according to the present embodiment is performed may be, for example, a "system in which some of the processes related to the information processing method according to the present embodiment are performed by one of apparatuses constituting the processing system, and the remaining processes excluding some of the processes related to the information processing method according to the present embodiment are performed by other apparatuses constituting the processing system."

(Program According to Present Embodiment)

When a program causing a computer to function as the information processing apparatus according to the present embodiment (for example, a program capable of executing the process related to the information processing method according to the present embodiment) is executed by a processor or the like in the computer, it is possible to improve the stability of the acquisition of the sampling data for the calibration of the line of sight.

Further, when a program causing a computer to function as the information processing apparatus according to the present embodiment is executed by a processor or the like in the computer, it is possible to obtain the effect obtained by the process related to the information processing method according to the present embodiment.

(Computer Readable Recording Medium Having Program According to Present Embodiment Recorded Therein)

In the above example, the program (computer program) causing the computer to function as the information processing apparatus according to the present embodiment is provided, but the present embodiment further provide a computer readable recording medium having the program recorded therein together.

Examples of the recording medium according to the present embodiment include a ROM, a non-volatile memory such as a flash memory, a magnetic recording medium such as a hard disk, and an arbitrary recording medium capable of storing a program such as an optical disk or a magneto-optical disk.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including a processing unit configured to perform a derivation process of deriving a relative positional relation between a user and a display screen such that a calibration position is within an angle of view of the display screen, the calibration position being stared by the user of a line of sight detection target when sampling data for calibration of a line of sight is acquired.

(2)

The information processing apparatus according to (1), in which the processing unit sets an intersection point of a reference vector corresponding to a forward direction of a face of the user and a plane including the display screen, as the calibration position, and in a case in which the calibration position is not within the angle of view of the display screen, the processing unit derives the relative positional relation such that the calibration position falls within the angle of view of the display screen.

(3)

The information processing apparatus according to (2), in which, in a case in which the calibration position is within the angle of view of the display screen, the processing unit causes an object indicating the calibration position to be displayed within the angle of view of the display screen.

(4)

The information processing apparatus according to (2) or (3), in which the processing unit specifies the plane on a basis of a predetermined object which is displayed on the display screen and detected from a captured image obtained by imaging in the forward direction from the face of the user.

(5)

The information processing apparatus according to any one of (2) to (4), in which the processing unit derives the relative positional relation by causing a derivation object for deriving the relative positional relation to be displayed on the display screen.

(6)

The information processing apparatus according to (5), in which the derivation object is an object indicating a direction in which the user moves or a direction in which the display screen is moved.

(7)

The information processing apparatus according to (6), in which the derivation object is displayed in an animated manner.

(8)

The information processing apparatus according to claim 1, in which the processing unit derives the relative positional relation by causing a voice for deriving the relative positional relation to be output from an audio output device.

(9)

The information processing apparatus according to any one of (1) to (7), in which the processing unit causes a notification indicating a derived state to be given to the user.

(10)

The information processing apparatus according to any one of (1) to (9), in which the processing unit performs the derivation process in a case in which a set start condition is determined to be satisfied.

(11)

The information processing apparatus according to any one of (1) to (10), in which the processing unit further performs a calibration process of calibrating a detection result of the line of sight on a basis of calibration information based on the acquired sampling data.

(12)

The information processing apparatus according to (11), in which the processing unit generates the calibration information on a basis of the sampling data, and calibrates the detection result of the line of sight on a basis of the generated calibration information.

(13)

An information processing method executed by an information processing apparatus, the method including a step of deriving a relative positional relation between a user and a display screen such that a calibration position is within an angle of view of the display screen, the calibration position being stared by the user of a line of sight detection target when sampling data for calibration of a line of sight is acquired.

(14)

A computer readable storage medium having a program stored therein, the program causing a computer to implement a function of deriving a relative positional relation between a user and a display screen such that a calibration position is within an angle of view of the display screen, the calibration position being stared by the user of a line of sight detection target when sampling data for calibration of a line of sight is acquired.

REFERENCE SIGNS LIST

100 information processing apparatus
102 communication unit
104 control unit
110 processing unit
112 derivation processing unit
114 calibration processing unit
116 stare detecting unit

The invention claimed is:

1. An information processing apparatus, comprising:
a processing unit configured to derive a relative positional relation between a user and a display screen, wherein
a calibration position is within an angle of view of the display screen,
the calibration position is stared by the user, and
the user is a line of sight detection target when sampling data for calibration of a line of sight is acquired.

2. The information processing apparatus according to claim 1, wherein
the processing unit is further configured to set an intersection point of a reference vector and a plane including the display screen, as the calibration position,
the reference vector corresponds to a forward direction of a face of the user, and
in a case in which the calibration position is outside the angle of view of the display screen, the processing unit is further configured to derive the relative positional relation such that the calibration position falls within the angle of view of the display screen.

3. The information processing apparatus according to claim 2, wherein
in a case in which the calibration position is within the angle of view of the display screen, the processing unit is further configured to display an object indicating the calibration position, and
the object is displayed within the angle of view of the display screen.

4. The information processing apparatus according to claim 2, wherein
the processing unit is further configured to specify the plane based on an object displayed on the display screen, and
the object is detected from a captured image obtained based on image capture in the forward direction from the face of the user.

5. The information processing apparatus according to claim 2, wherein the processing unit is further configured to derive the relative positional relation based on display of a derivation object for deriving the relative positional relation on the display screen.

6. The information processing apparatus according to claim 5, wherein the derivation object is an object indicating a direction in which the user moves or a direction in which the display screen is moved.

7. The information processing apparatus according to claim 6, wherein the derivation object is displayed in an animated manner.

8. The information processing apparatus according to claim 1, wherein the processing unit is further configured to derive the relative positional relation based on an output of a voice for deriving the relative positional relation from an audio output device.

9. The information processing apparatus according to claim 1, wherein
the processing unit is further configured to give a notification to the user, and
the notification indicates a derived state.

10. The information processing apparatus according to claim 1, wherein the processing unit is further configured to derive the relative positional relation based on a set start condition that is determined to be satisfied.

11. The information processing apparatus according to claim 1, wherein the processing unit is further configured to calibrate a detection result of the line of sight based on calibration information, and the calibration information is based on the acquired sampling data.

12. The information processing apparatus according to claim 11, wherein the processing unit is further configured to:

generate the calibration information based on the sampling data; and calibrate the detection result of the line of sight based on the generated calibration information.

13. An information processing method executed by an information processing apparatus, the method comprising:

deriving a relative positional relation between a user and a display screen, wherein a calibration position is within an angle of view of the display screen, the calibration position is stared by the user, and the user is a line of sight detection target when sampling data for calibration of a line of sight is acquired.

14. A non-transitory computer readable storage medium having stored therein, computer-executable instructions which, when executed by a computer, cause the computer to execute operations, the operations comprising:

deriving a relative positional relation between a user and a display screen, wherein a calibration position is within an angle of view of the display screen, the calibration position is stared by the user, and the user is a line of sight detection target when sampling data for calibration of a line of sight is acquired.

* * * * *